US008637250B2

(12) United States Patent
Jenison

(10) Patent No.: US 8,637,250 B2
(45) Date of Patent: Jan. 28, 2014

(54) SYSTEMS AND METHODS FOR POINT-OF-CARE AMPLIFICATION AND DETECTION OF POLYNUCLEOTIDES

(75) Inventor: Robert Delmar Jenison, Boulder, CO (US)

(73) Assignee: Great Basin Scientific, West Valley, UT (US)

( * ) Notice: Subject to any disclaimer, the term of this patent is extended or adjusted under 35 U.S.C. 154(b) by 609 days.

(21) Appl. No.: 12/779,397

(22) Filed: May 13, 2010

(65) Prior Publication Data

US 2010/0285479 A1 Nov. 11, 2010

Related U.S. Application Data

(63) Continuation of application No. 12/036,048, filed on Feb. 22, 2008, now abandoned.

(51) Int. Cl.
C12Q 1/68 (2006.01)
C12P 19/34 (2006.01)

(52) U.S. Cl.
USPC ............................ 435/6.12; 435/91.2

(58) Field of Classification Search
USPC .................................. 435/6.12, 91.2
See application file for complete search history.

(56) References Cited

U.S. PATENT DOCUMENTS

| | | | |
|---|---|---|---|
| 4,789,630 A | 12/1988 | Bloch et al. ................ 435/7 |
| 5,124,246 A | 6/1992 | Urdea et al. ................ 435/6 |
| 5,130,238 A | 7/1992 | Malek et al. ............... 435/91 |
| 5,176,995 A | 1/1993 | Sninsky et al. ............. 435/6 |
| 5,177,196 A | 1/1993 | Meyer, Jr. et al. .......... 536/22.1 |
| 5,185,439 A | 2/1993 | Arnold, Jr. et al. ......... 536/24.3 |
| 5,215,882 A | 6/1993 | Bahl et al. ................. 435/6 |
| 5,270,184 A | 12/1993 | Walker et al. .............. 435/91.2 |
| 5,283,174 A | 2/1994 | Arnold, Jr. et al. ......... 435/6 |
| 5,380,833 A | 1/1995 | Urdea ....................... 536/22.1 |
| 5,422,252 A | 6/1995 | Walker et al. .............. 435/91.2 |
| 5,455,166 A | 10/1995 | Walker ...................... 435/91.2 |
| 5,470,723 A | 11/1995 | Walker et al. .............. 435/91.2 |
| 5,498,392 A | 3/1996 | Wilding et al. ............. 422/68.1 |
| 5,514,785 A | 5/1996 | Van Ness et al. ........... 536/22.1 |
| 5,585,481 A | 12/1996 | Arnold, Jr. et al. ......... 536/25.33 |
| 5,637,469 A | 6/1997 | Wilding et al. ............. 435/7.21 |
| 5,639,604 A | 6/1997 | Arnold, Jr. et al. ......... 435/6 |
| 5,641,658 A | 6/1997 | Adams et al. .............. 435/91.2 |
| 5,660,989 A | 8/1997 | Cole et al. ................. 436/6 |
| 5,667,976 A | 9/1997 | Van Ness et al. ........... 435/6 |
| 5,681,702 A | 10/1997 | Collins et al. ............. 435/6 |
| 5,712,383 A | 1/1998 | Sheridan et al. ........... 436/24.3 |
| 5,714,320 A | 2/1998 | Kool ........................ 435/6 |
| 5,716,819 A | 2/1998 | Chatterjee ................. 435/194 |
| 5,747,244 A | 5/1998 | Sheridan et al. ........... 435/6 |
| 5,854,033 A | 12/1998 | Lizardi ..................... 435/91.2 |
| 5,919,626 A | 7/1999 | Shi et al. ................... 435/6 |
| 5,955,377 A | 9/1999 | Maul et al. ................ 436/518 |
| 5,994,065 A | 11/1999 | Van Ness ................... 435/6 |
| 6,013,789 A | 1/2000 | Rampal .................... 536/25.3 |
| 6,027,879 A | 2/2000 | Lucas et al. ................ 435/6 |
| 6,048,695 A | 4/2000 | Bradley et al. ............. 435/6 |
| 6,060,237 A | 5/2000 | Nygren et al. ............. 435/6 |
| 6,060,246 A | 5/2000 | Summerton et al. ........ 435/6 |
| 6,087,133 A | 7/2000 | Dattagupta et al. ......... 435/91.1 |
| 6,235,502 B1 | 5/2001 | Weissman et al. .......... 435/91.1 |
| 6,248,521 B1 | 6/2001 | Van Ness et al. ........... 435/6 |
| 6,251,639 B1 | 6/2001 | Kurn ........................ 435/91.2 |
| 6,268,490 B1 | 7/2001 | Imanishi et al. ........... 536/23.1 |
| 6,306,665 B1 | 10/2001 | Buck et al. ................ 436/530 |
| 6,344,329 B1 | 2/2002 | Lizardi ..................... 435/6 |
| 6,355,429 B1 | 3/2002 | Nygren et al. ............. 436/6 |
| 6,410,278 B1 | 6/2002 | Notomi et al. ............. 435/91.2 |
| 6,528,264 B1 | 3/2003 | Pal et al. ................... 435/6 |
| 6,531,302 B1 | 3/2003 | Nerenberg et al. ......... 435/91.2 |
| 6,555,349 B1 | 4/2003 | O'Donnell ................. 435/91.2 |
| 6,642,000 B1 | 11/2003 | Strizhkov et al. .......... 435/6 |
| 6,649,378 B1 | 11/2003 | Kozwich et al. ........... 435/91.2 |
| 6,660,517 B1 | 12/2003 | Wilding et al. ............. 435/289.1 |

(Continued)

FOREIGN PATENT DOCUMENTS

| | | |
|---|---|---|
| KR | 10-2008-0029233 | 4/2008 |
| WO | WO 03/046508 A2 | 6/2003 |

(Continued)

OTHER PUBLICATIONS

International Search Report/Written Opinion of PCT/US2009/034685 dated Oct. 2, 2009 (22-pages).

Adessi, Celine, et al., *Solid Phase DNA Amplification: Characterization of Primer Attachment and Amplification Mechanisms*, Nucleic Acids Research, (2000), vol. 28, No. 20, e87 (pp. 1-8).

An, Lixin, et al., "*Characterization of a Thermostable UvrD Helicase and Its Participation in Helicase-dependent Amplifications*", The Journal of Biological Chemistry, (Aug. 2005), vol. 280, No. 32, pp. 28952-28958.

Beier, Markus, et al., *Versatile Derivatisation of Solid Support Media for Covalent Bonding on DNA-Microchips*, Nucleic Acids Research, (1999), vol. 27, No. 9, pp. 1970-1977.

(Continued)

*Primary Examiner* — Teresa E Strzelecka
*Assistant Examiner* — Joyce Tung
(74) *Attorney, Agent, or Firm* — Brinks Gilson & Lione; Ryan L. Marshall

(57) ABSTRACT

Composition and methods for amplifying and detecting solution-state polynucleotide targets in a single device are described. In one aspect, a method for a coupled isothermal amplification and detection process utilizes a coated solid support, including a solid substrate, a cationic layer, and a plurality of target-specific probes attached to the coated solid support. Polynucleotide targets in the sample are amplified by an isothermal amplification process involving in situ hybridization onto the coated solid support. The entire process can be carried out with a high degree of specificity under low salt conditions in less than one hour. Further aspects of the present invention include methods for coupled hybridization/detection of polynucleotide targets, coated silicon biosensors optimized for use with the coupled detection systems to provide visual detection of polynucleotide targets under visible light conditions, and kits for practicing in the above described methods.

24 Claims, 9 Drawing Sheets

(56) References Cited

U.S. PATENT DOCUMENTS

| | | | |
|---|---|---|---|
| 6,670,461 B1 | 12/2003 | Wengel et al. | 536/23.1 |
| 6,692,918 B2 | 2/2004 | Kurn | 435/6 |
| 6,743,605 B1 | 6/2004 | Rabbani et al. | 435/91.2 |
| 6,764,821 B1 | 7/2004 | Rabbani et al. | 435/6 |
| 6,783,938 B2 | 8/2004 | Nygren et al. | 435/6 |
| 6,787,312 B2 | 9/2004 | Bao et al. | 435/6 |
| 6,861,214 B1 | 3/2005 | Rampal et al. | 435/6 |
| 6,903,206 B1 | 6/2005 | Becker et al. | 536/24.3 |
| 6,905,816 B2 | 6/2005 | Jacobs et al. | 435/5 |
| 6,929,915 B2 | 8/2005 | Benkovic et al. | 435/6 |
| 6,946,251 B2 | 9/2005 | Kurn | 435/6 |
| 6,977,148 B2 | 12/2005 | Dean et al. | 435/6 |
| 7,005,265 B1 | 2/2006 | Fan et al. | 435/6 |
| 7,264,930 B2 | 9/2007 | Rabbani et al. | 435/6 |
| 7,270,981 B2 | 9/2007 | Armes et al. | 435/91.2 |
| 7,282,328 B2 | 10/2007 | Kong et al. | 435/6 |
| 7,291,471 B2 | 11/2007 | Sampson et al. | 435/6 |
| 2001/0036634 A1 | 11/2001 | Chow et al. | 435/6 |
| 2002/0025519 A1* | 2/2002 | Wright et al. | 435/6 |
| 2002/0120127 A1* | 8/2002 | Church et al. | 536/25.3 |
| 2002/0172969 A1 | 11/2002 | Burns et al. | 435/6 |
| 2003/0105320 A1 | 6/2003 | Becker et al. | 536/24.3 |
| 2003/0134299 A1 | 7/2003 | Hogan et al. | 435/6 |
| 2003/0148304 A1 | 8/2003 | Liang et al. | 435/6 |
| 2003/0207296 A1 | 11/2003 | Park et al. | 435/6 |
| 2004/0018507 A1 | 1/2004 | Joos et al. | 435/6 |
| 2004/0043508 A1 | 3/2004 | Frutos et al. | 436/518 |
| 2004/0053290 A1 | 3/2004 | Terbrueggen et al. | 435/6 |
| 2004/0115643 A1 | 6/2004 | Lizardi et al. | 435/6 |
| 2004/0171001 A1 | 9/2004 | Leclerc et al. | 435/6 |
| 2004/0241713 A1 | 12/2004 | Mirzabekov et al. | 435/6 |
| 2005/0053944 A1 | 3/2005 | Fuchs et al. | 435/6 |
| 2005/0069926 A1 | 3/2005 | Cole et al. | 435/6 |
| 2005/0106576 A1 | 5/2005 | Akhavan-Tafti et al. | 435/6 |
| 2005/0112631 A1 | 5/2005 | Piepenburg et al. | 435/6 |
| 2005/0181394 A1 | 8/2005 | Steemers et al. | 435/6 |
| 2005/0196760 A1 | 9/2005 | Pemov et al. | 435/6 |
| 2005/0196779 A1 | 9/2005 | Ho et al. | 435/6 |
| 2006/0035275 A1 | 2/2006 | Ward et al. | 435/6 |
| 2006/0068417 A1 | 3/2006 | Becker et al. | 435/6 |
| 2006/0105337 A1 | 5/2006 | Warner et al. | 435/6 |
| 2006/0147943 A1 | 7/2006 | Lewis | 435/6 |
| 2006/0147958 A1 | 7/2006 | Koshinsky et al. | 435/6 |
| 2006/0154286 A1 | 7/2006 | Kong et al. | 435/6 |
| 2006/0240462 A1 | 10/2006 | Todd et al. | 435/6 |
| 2006/0257874 A1 | 11/2006 | Tisi et al. | 435/6 |
| 2007/0009884 A1 | 1/2007 | Stoughton et al. | 435/5 |
| 2007/0026391 A1 | 2/2007 | Stoughton et al. | 435/5 |
| 2007/0037175 A1 | 2/2007 | Leproust et al. | 435/6 |
| 2007/0128589 A1 | 6/2007 | Sanders et al. | 435/5 |
| 2007/0154899 A1 | 7/2007 | Coull et al. | 435/6 |
| 2007/0154922 A1 | 7/2007 | Collier et al. | 435/6 |
| 2007/0166725 A1 | 7/2007 | McBride et al. | 435/6 |
| 2007/0166741 A1 | 7/2007 | Heil et al. | 435/6 |
| 2007/0178470 A1 | 8/2007 | Bissonnette et al. | 435/6 |
| 2007/0202522 A1 | 8/2007 | Salinas | 435/6 |
| 2007/0212695 A1 | 9/2007 | Aivazachvili et al. | 435/6 |
| 2007/0218459 A1 | 9/2007 | Miller et al. | 435/6 |
| 2007/0218464 A1 | 9/2007 | Nakamura et al. | 435/6 |
| 2007/0248964 A1 | 10/2007 | Gao et al. | 435/6 |
| 2007/0259359 A1 | 11/2007 | Briman et al. | 435/6 |
| 2007/0269799 A9 | 11/2007 | Zhang | 435/6 |
| 2008/0003693 A1 | 1/2008 | Torres | 436/501 |
| 2008/0293045 A1 | 11/2008 | Piepenburg | 435/6 |
| 2009/0130657 A1 | 5/2009 | Millar | 435/6 |
| 2009/0221096 A1 | 9/2009 | Torres | 436/501 |

FOREIGN PATENT DOCUMENTS

| | | |
|---|---|---|
| WO | WO 03/072805 A2 | 9/2003 |
| WO | WO 2004/027025 A2 | 4/2004 |
| WO | WO 2005/056827 A1 | 6/2005 |
| WO | WO 2007/033283 A2 | 3/2007 |
| WO | WO 2007/070832 A1 | 6/2007 |
| WO | WO 2009/070640 A2 | 6/2009 |
| WO | WO 2009/070742 A2 | 6/2009 |

OTHER PUBLICATIONS

Belosludtsev, Yrui, et al., "*DNA Microarrays Based on Noncovalent Oligonucleotide Attachment and Hybridization in Two Dimensions*," Analytical Biochemistry, (2001), vol. 292, pp. 250-256.

Bista, Bipin Raj, et al., "*Development of a Loop-Mediated Isothermal Amplification Assay for Rapid Detection of BK Virus*", Journal of Clinical Microbiology, (May 2007), pp. 1581-1587.

Boehme, Catharina C., et al., "*Operational Feasibility of Using Loop-Mediated Isothermal Amplification for Diagnosis of Pulmonary Tuberculosis in Microscopy Centers of Developing Countries*", Journal of Clinical Microbiology, (Jun. 2007), pp. 1936-1940.

Brandt, Ole, et al., "*PNA Microarrays for Hybridization of Unlabelled DNA Samples*", Nucleic Acids Research, (2003), vol. 31, No. 19, e119 pp. 1-9.

Carter, Darren, et al., "*Lateral Flow Microarrays: A Novel Platform for Rapid Nucleic Acid Detection Based on Miniaturized Lateral Flow Chromatography*", Nucleic Acids Research, (2007), vol. 35, No. 10, e74 pp. 1-11.

Cheng, Jing, et al., "*Chip PCR. II. Investigation of Different PCR Amplification Systems in Microfabricated Silicon-Glass Chips*", Nucleic Acids Research, (1996), vol. 24, No. 2, pp. 380-385.

Chiu, Sung-Kay, et al., "*Synergistic Effects of Epoxy- and Amine-Silanes on Microarray DNA Immobilization and Hybridization*", Biochem. J., (2003), vol. 374, pp. 625-632.

Chung, Yung-Chiang, et al., "*Microfluidic Chip for Fast Nucleic Acid Hybridization*", The Royal Society of Chemistry, (2003), Lab Chip, vol. 3, pp. 228-233.

Cosentino, Lisa A., et al., "*Detection of Chlamydia trachomatis and Neisseria gonhorrhoeae by Strand Displacement Amplification and Relevance of the Amplification Control for Use with Vaginal Swab Specimens*", Journal of Clinical Microbiology, (Aug. 2003), vol. 41, No. 8, pp. 3592-3596.

De Barr, Michael P., et al., "*One-Tube Real-Time Isothermal Amplification Assay to Identify and Distinguish Human Immunodeficiency Virus Type 1 Subtypes A, B, and C and Circulating Recombinant Forms AE and AG*", Journal of Clinical Microbiology, (May 2001), vol. 39, No. 5, pp. 1895-1902.

Diehl, Frank, et al., "*Manufacturing DNA Microarrays of High Spot Homogeneity and Reduced Background Signal*", Nucleic Acids Research, (2001), vol. 29, No. 7, e38 pp. 1-5.

Dolan, Patricia L. et al., "*Robust and Efficient Synthetic Method for Forming DNA Microarrays*", Nucleic Acids Research, (2001), vol. 29, No. 21, e107 pp. 1-8.

Edman, Carl F., et al., "*Electric Field Directed Nucleic Acid Hybridization on Microchips*", Nucleic Acids Research, (1997), vol. 25, No. 24, pp. 4907-4914.

Eisenstein, Michael, "*Breaking the Cycle*", Nature/Methods Jul. 27, 2004, pp. 1-2. http://www.nature.com/nmeth/journal/v1/n1/pf/neth031.html.

Eoff, Robert L., et al., "*Chemically Modified DNA Substrates Implicate the Importance of Electrostatic Interactions for DNA Unwinding by Dda Helicase*", Biochemistry, (2005), vol. 44, pp. 666-674.

Ferrer, Elisenda et al., "*Synthesis and Hybridization of Properties of DNA-PNA Chimeras Carrying 5Bromouracil and 5-Methylcytosine*", Bioorganic & Medicinal Chemistry, (Feb. 2000), vol. 8, No. 2, pp. 291-297. Abstract.

Fixe, F., et; al., "*An On-Chip Thin-Film Photodetector for the Quantification of DNA Probes and Targets in Microarrays*", Nucleic Acids Res. (2004) vol. 32, No. 9, p. e70 pp. 1-9.

Gao, Huafang, et al., "*Comparison of Different Methods for Preparing Single Stranded DNA for Oligonucleotide Microarray*", Analytical Letters, vol. 33, No. 13, 2003, pp. 2849-2863.

Gaylord, Brent S., "*DNA detection using water-soluble conjugated polymers and peptide nucleic acid probes*", PNAS, (Aug. 2002), vol. 99, No. 17, pp. 10954-10957.

(56) References Cited

OTHER PUBLICATIONS

Gill, Pooria, et al., "Detection of Helicobacter Pylori by Enzyme-Linked Immunosorbent Assay of Thermophilic Helicase-Dependent Isothermal DNA Amplification", ScienceDirect Diagnostic Microbiology and Infectious Disease (2007) vol. 59, pp. 243-249.

Goldmeyer, James, et al., "Development of a Novel One-Tube Isothermal Reverse Transcription Thermophilic Helicase-Dependent Amplification Platform for Rapid RNA Detection", Journal of Molecular Diagnostics, (Nov. 2007), vol. 9, No. 5, pp. 639-644.

Goldmeyer, James, et al., "Identification of Staphylococcus aureus and Determination of Methicillin Resistance Directly from Positive Blood Cultures by Isothermal Amplification and a Disposable Detection Device", Journal of Clinical Microbiology, vol. 46, No. 4, Apr. 2008, pp. 1534-1536.

Guo, Zhen, et al., "Oligonucleotide Arrays for High-Throughput SNPs Detection in the MHC Class I Genes: HLA-B as a Model System", Genome Research, (2002) vol. 12, pp. 447-457.

Gusev, Yuriy, et al., "Rolling Circle Amplification a New Approach to Increase Sensitivity for Immunohistochemistry and Flow Cytometry", American Journal of Pathology, (Jul. 2001), vol. 159, No. 1, pp. 63-69.

Han, Tao, et al., "Improvement in the Reproducibility and Accuracy of DNA Microarray Quantification by Optimizing Hybridization Conditions", BMC Bioinformatics, (2006), 7(Suppl2):S17, pp. 1-13.

Handyside, Alan H., et al., "Isothermal Whole Genome Amplification From Single and Small Numbers of Cells: A New Era for Preimplantation Genetic Diagnosis of Inherited Disease", Molecular Human Reproduction, (2004), vol. 10, No. 10, pp. 767-772.

Hessner, Martin, J. et al., "Immobilized Probe and Glass Surface Chemistry as Variables in Microarray Fabrication", BMC Genomics, (2004), vol. 5:53, pp. 1-8.

Holding, Cathy, "Isothermal Amplification Kits of Lyophilized Reagents for Field Use Could Appear Soon", The Scientist, (Jul. 14, 2004), pp. 1-2. http://www.biomedcentral.com/news/20040714/02/.

Hong, Bong Jin, et al., "DNA Microarrays on Nanoscale-Controlled Surface", Nucleic Acids Research, (2005), vol. 33, No. 12, e106 pp. 1-8.

Huletsky, A., et al., "New Real-Time PCR Assay for Rapid Detection of Methicillin-Resistant Staphylococcus aureus Directly From Specimens Containing a Mixture of Staphylococci", Journal of Clinical Microbiology, (May 2004), vol. 42, No. 5, pp. 1875-1884.

Jean, Julie et al., "Rapid Detection of Human Rotavirus Using Colorimetric Nucleic Acid Sequence-Based Amplification (NASBA)-Enzyme-Linked Immunosorbent Assay in Sewage Treatment Effluent", FEMS Microbiology Letters 210 (2002) pp. 143-147.

Jenison, Robert, et al., "Interference-based Detection of Nucleic Acid Targets on Optically Coated Silicon", Nature Biotechnology, (Jan. 2001), vol. 19, pp. 62-65.

Jenison, Robert, et al., "Silicon-Based Biosensors for Rapid Detection of Protein or Nucleic Acid Targets", Clinical Chemistry, (2001), vol. 47:10, pp. 1894-1900.

Jenison, Robert, et al., "Thin-Film Biosensor for Rapid Detection of mecA From Methicillin-Resistant Staphylococcus aureus", Clinical Chemistry, (2000), vol. 46, No. 9, pp. 1501-1504.

Jenison, Robert, et al., "Thin-Film Technology for Direct Visual Detection of Nucleic Acid Sequences: Applications in Clinical Research", Future Drugs, Ltd., Expert Rev. Mol. Diagn. (2006), vol. 6:1, pp. 1-11.

Kajiyama, Tomoharu, et al., "Genotyping on a Thermal Gradient DNA Chip", Genome Res. (2003), vol. 13, pp. 467-475. Article cited in http://www.genome.org/cgi/content/full/13/3/467#otherarticles.

Kamisetty, Nagendra Kumar, et al., "Development of Stable DNA Microarray Platforms Suitable for Quantitative Analysis", Nucleic Acids Symposium Series, (2007), No. 51, pp. 327-328.

Kong, Huimin et al., "New Isothermal Molecular Diagnostic Platforms", Medical Devicelink, Nov./Dec. 2007, pp. 1-6. http://www.devicelink.com/grabber.php3?URL=http://www.devicelink.com/ivdt/archive/07/11/009.html.

Kricka, Larry J., et al., "Fabrication of Plastic Microchips by Hot Embossing", The Royal Society of Chemistry, (2002), Lab Chip, vol. 2, pp. 1-4.

Kumar, Anil, et al., "Silanized Nucleic Acids: A General Platform for DNA Immobilization", Nucleic Acids Research, (2000), vol. 28, No. 14, e71 pp. 1-6.

Kumar, P, et al., Construction of Oligonucleotide Arrays on a Glass Surface Using a Heterobifunctional Reagent, N-(2-trifluoroethanesulfonatoethyl)-N-(methyl)-triethoxysilylpropyl-3-amine (NTMTA), Nucleic Acids Research, (2004), vol. 32, No. 10, e80 pp. 1-9.

Kurn, Nurith, et al., "Novel Isothermal, Linear Nucleic Acid Amplification Systems for Highly Multiplexed Applications", Clinical Chemistry, (2005), vol. 51:10, pp. 1973-1981.

Lai, Rebecca Y., et al., "Rapid, Sequence-Specific Detection of Unpurified PCR Amplicons via a Reusable, Electrochemical Sensor", PNAS, (Mar. 2006), vol. 103, No. 11, pp. 4017-4021.

Le Berre, Veronique, et al., "Dendrimeric Coating of Glass Slides for Sensitive DNA Microarrays Analysis", Nucleic Acids Research, (2003), vol. 31, No. 16, e88 pp. 1-8.

Lee, Thomas Ming-Hung, et al., "Microfabricated PCR-electrochemical device for simultaneous DNA amplification and detection" The Royal Society of Chemistry (2003), Lab Chip, vol. 3, pp. 100-105.

Lemeshko, S.V., et al., "Oligonucleotides Form a Duplex with Non-Helical Properties on a Positively Charged Surface", Nucleic Acids Research, (2001), vol. 29, No. 14, pp. 3051-3058.

Li, Ying, et al., "Genotyping of HFE Mutations Responsible for Hereditary Hemochromatosis Using Isothermal Helicase Dependent Amplification (HDA) Technology", Biohelix, (1p).

Little, Michael C., et al., "Amplified DNA Probes", Clinical Chemistry, (1999), vol. 45:6, pp. 777-784.

Liu, Robin Hui, et al., "Self-Contained, Fully Integrated Biochip for Sample Preparation, Polymerase Chain Reaction Amplification, and DNA Microarray Detection", Anal. Chem. (2004), vol. 76, pp. 1824-1831.

Lou, Xing Jian, et al., "Increased amplification efficiency of Microchip-Based PCR by Dynamic Surface Passivation", BioTechniques, (2004), vol. 36, No. 2, pp. 248-251.

Lutz-Bonengel, Sabine, et al., "Low Volume Amplification and Sequencing of Mitochondrial DNA on a Chemically Structured Chip", Int. J. Legal Med., (2007), vol. 121, pp. 68-73.

Macanovic, A., et al., "Impedance-based Detection of DNA Sequences Using a Silicon Transducer with PNA as the Probe Layer", Nucleic Acids Research, (2004), vol. 32 No. 2, e20 pp. 1-7.

Mackintosh, Samuel G., et al., "DNA Unwinding and Protein Displacement by Superfamily 1 and Superfamily 2 Helicases", Nucleic Acids Research, (2006), vol. 34, No. 15, pp. 4154-4159.

Maruyama, Fumito, et al., "Detection of Bacteria Carrying the stx2 Gene by In Situ Loop-mediated Isothermal Amplification", Applied and Environmental Microbiology, (Aug. 2003), vol. 69, No. 8, pp. 5023-5028.

Masuko, Masayuki, "Hybridization of an Immobilized PNA Probe With Its Complementary Oligodeoxyribonucleotide on the Surface of Silica Glass", Nucleic Acids Research Supplement, (2003), No. 3, pp. 145-146.

McGlennen, Ronald C., "Miniaturization Technologies for Molecular Diagnostics", Clinical Chemistry, (2001), vol. 47:3, pp. 393-402.

Menard, C., et al., "Real-Time Detection of Clinically Relevant Bacterial Pathogens: Description and Preliminary Performances of a New System", Infectio Diagnostics (I.D.I.) Inc., Quebec City, Quebec, Canada, pp. 1-4. http://www.cepheid.com/media/files/abstracts-and-presentations/pathogen_detection.pdf.

Mitterer, Georg, et al., "Microarray-Based Identification of Bacteria in Clinical Samples by Solid-Phase PCR Amplification of 23S Ribosomal DNA Sequences", Journal of Clinical Microbiology, (Mar. 2004), vol. 42, No. 3, pp. 1048-1057.

Mori, Nobuo, et al., "Development of a New Method for Diagnosis of Rubella Virus Infection by Reverse Transcription-Loop-Mediated Isothermal Amplification", Journal of Clinical Microbiology, (Sep. 2006), vol. 44, No. 9, pp. 3268-3273.

(56) References Cited

OTHER PUBLICATIONS

Mori, Yasuyoshi, et al., "*Sequence Specific Visual Detection of LAMP Reactions by Addition of Cationic Polymers*", BMC Biotechnology, (2006), 6:3, pp. 1-10.

Nanduri, Bindu, et al., "*Measurement of Steady-State Kinetic Parameters for DNA Unwinding by the Bacteriophase T4 Dda Helicase: Use of Peptide Nucleic Acids to Trap Single-Stranded DNA Products of Helicase Reactions*", Nucleic Acids Research, (2001), vol. 29, No. 13, pp. 2829-2835.

Neuzil, Pavel, et al., "*Ultra Fast Miniaturized Real-Time PCT: 40 Cycles in Less Than Six Minutes*", Nucleic Acids Research, (2006), vol. 34, No. 11, e77 pp. 1-9.

Notomi, Tsugunori, et al., "*Loop-Mediated Isothermal Amplification of DNA*", Nucleic Acids Research, (2000), vol. 28, No. 12, e63 pp. 1-7.

Ostroff, Rachel M., et al., "*Fixed Polarizer Ellipsometry for Simple and Sensitive Detection of Thin Films Generated by Specific Molecular Interactions: Applications in Immunoassays and DNA Sequence Detection*", Clinical Chemistry, (1998), vol. 44:9, pp. 2031-2035.

Ostroff, Rachel M., et al., "*Thin Film Biosensor for Rapid Visual Detection of Nucleic Acid Targets*", Clinical Chemistry, (1999), vol. 45:9, pp. 1659-1664.

Pasternak, Rafael, et al., "*Evaluation of the Gen-Probe Chlamydia trachomatis Transcription-Mediated Amplification Assay With Urine Specimens From Women*", Journal of Clinical Microbiology, (Mar. 1997), vol. 35, No. 3, pp. 676-678.

Pemov, A., et al., "*DNA Analysis With Multiplex Microarray-Enhanced PCR*", Nucleic Acids Research, (2005), vol. 33, No. 2, e11 pp. 1-9.

Piepenburg, Olaf, et al., "*Biochemical Solutions for Portable Nucleic Acid Testing*", Electronics Meets Biology, (2007), pp. 32-35. www.bioworld-europe.com. http://www.asm-scientific.co.uk/BWE_1_07_p.32-35.pdf.

Piepenburg, Olaf, et al., "*DNA Detection Using Recombination Proteins*", PLoS Biology, (Jul. 2006), vol. 4, No. 7, pp. 1115-1121.

Raymond, Frederic, R., et al., "*Detection of Target DNA Using Fluorescent Cationic Polymer and Peptide Nucleic Acid Probes on Solid Support*", BMC Biotechnology, (2005), vol. 5:10, pp. 1-5.

Redkar, Rajendra J., et al., "*Signal and Sensitivity Enhancement Through Optical Interference Coating for DNA and Protein Microarray Applications*", Journal of Biomolecular Techniques, (2006), vol. 17, pp. 122-130.

Salinas, Frank, et al., "*Characterization of Bacteriophase T4-Coordinated Leading- and Lagging-Strand Synthesis on a Minicircle Substrate*", PNAS, (Jun. 2000), vol. 97, No. 13, pp. 7196-7201.

Sato, Kiichi, et al., "*Integration of Chemical and Biochemical Analysis Systems into a Glass Microchip*", Analytical Sciences, (Jan. 2003), vol. 19, pp. 15-19.

Schaad, N.W., et al., "*On-Site One Hour PCR Diagnosis of Bacterial Diseases*", Cepheid.com 2001, http://www.cepheid.com/Sites/cepheid/litpdfs/watermelon_fruit_blotch.pdf.

Shoffner, Mann A., et al., "*Chip PCR. I. Surface Passivation of Microfabricated Silicon-Glass Chips for PCR*", Nucleic Acids Research, (1996), vol. 24, No. 2, pp. 375-379.

Singh, Ruchira, et al., "*Microarray-Based Comparison of Three Amplification Methods for Nanogram Amounts of Total RNA*", Am. J. Physio. Cell Physiol., (Dec. 2005), vol. 288, pp. 1179-1189.

Smolina, Irina V., "*End Invasion of Peptide Nucleic Acids (PNAs) With Mixed-Base Composition into Linear DNA Duplexes*", Nucleic Acids Research, (2005), vol. 33, No. 17, e146 pp. 1-9.

Sosnowski, Ronald G., "*Rapid Determination of Single Base Mismatch Mutations in DNA Hybrids by Direct Electric Field Control*", Biochemistry, (1997), vol. 94, pp. 1119-1123.

Steel, A.B., et al., "*Immobilization of Nucleic Acids at Solid Surfaces: Effect of Oligonucleotide Length on Layer Assembly*", Biophysical Journal, (Aug. 2000), vol. 79, pp. 975-981.

Tackett, Alan, J., et al., "*Unwinding of Nucleic Acids by HCV NS3 Helicase is Sensitive to the Structure of the Duplex*", Nucleic Acids Research, (2001), vol. 29, No. 2, pp. 565-572.

Taylor, Theresa B., et al., "*Optimization of the Performance of the Polymerase Chain Reaction in Silicon-Based Microstructures*", Nucleic Acids Research, (1997), vol. 25, No. 15, pp. 3164-3168.

Taylor, Scott, et al., "*Impact of Surface Chemistry and Blocking Strategies on DNA Microarrays*", Nucleic Acids Research, (2003), vol. 31, No. 16 pp. e87 pp. 1-19.

Teo, I.A., et al., "*LighCycler qPCR Optimisation for Low Copy Number Target DNA*", Journal of Immunological Methods, (2002), vol. 270, pp. 119-133.

Uno, Takeshi, et al., "*Peptide-Nucleic Acid-Modified Ion-Sensitive Field-Effect Transistor-Based Biosensor for Direct Detection of DNA Hybridization*", Anal. Chem., (2007), vol. 79, pp. 52-59.

Van Dyck, E., et al., "*Detection of Chlamydia trachomatis and Neisseria gonorrhoeae by Enzyme Immunoassay, Culture, and Three Nucleic Acid Amplification Tests*", Journal of Clinical Microbiology, (May 2001), vol. 39, No. 5, pp. 1751-1756.

Vincent, Myriam, et al., "*Helicase-Dependent Isothermal DNA Amplification*", European Molecular Biology Organization, (2004), vol. 5, No. 8, pp. 795-800.

Vora, Gary J., et al., "*Nucleic Acid Amplification Strategies for DNA Microarray-Based Pathogen Detection*", Applied and Environmental Microbiology, (May 2004), vol. 70, No. 5, pp. 3047-3054.

Walker, Terrance G., "*Isothermal in vitro Amplification of DNA by a Restriction Enzyme/DNA Polymerase System*", Proc. Natl. Acad. Sci., (Jan. 1992), vol. 89, pp. 392-396.

Wang, Wei, et al., "*Silicon Inhibition Effects on the Polymerase Chain Reaction: A Real-Time Detection Approach*", Wiley Periodicals, Inc., (2005), pp. 29-34; www.interscience.wiley.com.

Wang, Xujing, et al., "*Quantitative Quality Control in Microarray Image Processing and Data Acquisition*", Nucleic Acids Research, (2001), vol. 29, No. 15, e75 pp. 1-8.

Westin, Lorelei, et al., "*Antimicrobial Resistance and Bacterial Identification Utilizing a Microelectronic Chip Array*", Journal of Clinical Microbiology, (Mar. 2001), vol. 39, No. 3, pp. 1097-1104.

Wilding, Peter, et al., "*PCR in a Silicon Microstructure*", Clin. Chem., (1994), vol. 40, No. 9, pp. 1815-1818.

Xu, H.Q., et al., "*Simultaneously Monitoring DNA Binding and Helicase-Catalyzed DNA Unwinding by Fluorescence Polarization*", Nucleic Acids Research, (2003), vol. 31, No. 4, e70 pp. 1-8.

Xu, Qingchai, et al., "*Protein and Chemical Microarrays—Powerful Tools for Proteomics*", Journal of Biomedicine and Biotechnology, (2003), 2003:5, pp. 257-266; http:/jbb.hindawi.com.

Xu, Yan, et al., "*Simultaneous Amplification and Screening of Whole Plasmids Using the T7 Bacteriophage Replisome*", Nucleic Acids Research, (2006), vol. 34, No. 13, e98 pp. 1-9.

Yao, Danfeng, et al., "*Surface Density Dependence of PCR Amplicon Hybridization on PNA/DNA Probe Layers*", Biophysical Journal, (Apr. 2005), vol. 88, pp. 2745-2751.

Yeung, Siu-Wai, et al., "*A DNA Biochip for On-the-Spot Multiplexed Pathogen Identification*", Nucleic Acids Research, (2006), vol. 34, No. 18, e118 pp. 1-8.

Yuen, Po Ki, et al., "*Microchip Module for Blood Sample Preparation and Nucleic Acid Amplification Reactions*", Genome Research, (2001), vol. 11, pp. 405-412; http://www.genome.org/cgi/content/full/11/3/405#otherarticles.

Zhang, Wandi, et al., "*Detection of Chlamydia trachomatis by Isothermal Ramification Amplification Method: a Feasibility Study*", Journal of Clinical Microbiology, (Jan. 2002), vol. 40, No. 1, pp. 128-132.

Zhong, Xiao-bo, et al., *Single-Nucleotide Polymorphism Genotyping on Optical Thin-Film Biosensor Chips*, PNAS, vol. 100, No. 20, Sep. 30, 2003, pp. 11559-11564.

Zhong, Xiao-bo, et al., "*Simultaneous Detection of Microsatellite Repeats and SNPs in the Macrophage Migration Inhibitory Factor (MIF) Gene by Thin-Film Biosensor Chips and Application to Rural Field Studies*", Nucleic Acids Research, (2005), vol. 33, No. 13, e121 pp. 1-8.

IsoAmp tHDA Kit, (tHDA:thermophilic Helicase-Dependent Amplification), Biohelix, Catalog #H0100S, Instruction Manual, (2p). Date unknown. http://www.neb.com/nebecomm/ManualFiles/manualH0100.pdf.

(56) References Cited

OTHER PUBLICATIONS

IsoAmpll Universal tHDA Kit, (tHDA:thermophilic Helicase-Dependent Amplification), Catalog #H0110S, Biohelix, Instruction Manual, (4p). Date Unknown. http://www.biohelix.com/pdf/H0110S_full_version_BH.pdf.

Rapisome pWGA Kit (pWGA:primase-based Whole Genome Amplification), Biohelix, Catalog #H0300S, 2p. http://www.biohelix.com/pdf/H0300S_pWGA_manual.pdf.

Exiqon—Locked Nucleic Acid—LNA TM, Color Brochure 4 p. www.exigon.com.

Nature Publishing Group Research Highlights: Diagnostics: Cool Amplification of DNA; EMBO Rep. doi:1.1038/sj.embor.7400200 (2004). Angela K. Eggleston, p. 416.

Xpert MRSA, Redefining Active MRSA Surveillance Testing, Brochure 4p. www.cepheid.com.

* cited by examiner

| Input Copies | Primer Set | | | |
|---|---|---|---|---|
| | J | L | Q | P |
| 100 | 24.54 | 25.83 | 33.03 | |
| 1000 | 23 | 23.22 | 28.97 | |
| 10000 | 20.73 | 20.94 | 24.27 | 56.46 |
| 100000 | 17.9 | 18.01 | 21.74 | 52.93 |
| 1000000 | 14.63 | 15.56 | 18.16 | 41.01 |
| double time | 1.1 min | 1.1 min | 1.6 min | 3.4 min |

| Primer or Probe | Sequence |
|---|---|
| mecA L FWD | TGGATAGACGTCATATGAAGGTGTGCT (SEQ ID NO. 1) |
| mecA L REV | 5'-BT-ATTATGGCTCAGGTACTGCTATCCACC (SEQ ID NO. 2) |
| mecA J FWD | TGGATAGACGTCATATGAAGGTGTGCT (SEQ ID NO. 3) |
| mecA J REV | 5'-BT-TGATTATGGCTCAGGTACTGCTATCC (SEQ ID NO. 4) |
| mecA1703 CP | 5'ILink12/iSp18/CAAGTGCTAATAATTCACCTGTTTG (SEQ ID NO. 5) |
| mecA Q FWD | CAAACTACGGTAACATTGATCGCAACG (SEQ ID NO. 6) |
| mecA Q REV | 5'-BT-ATGCTTTGGTCTTTCTGCATTCCTG (SEQ ID NO. 7) |
| mecA1653 CP | 5'ILink12/iSp18/AAACAAACTACGGTAACATTGA (SEQ ID NO. 8) |
| APOB4 rev | 5'-BT-CAGTGTATCTGGAAAGCCTACAGGACACCAAAA (SEQ ID NO. 9) |
| APOB FWD 3 | CTTCATGTGAGCCAAAGATGCTGAAC (SEQ ID NO. 10) |
| APOB-CP1 | 5'ILink12/iSp18/AATTTGGCCTTCATGTGAGC (SEQ ID NO. 11) |

FIGURE 9

SYSTEMS AND METHODS FOR POINT-OF-CARE AMPLIFICATION AND DETECTION OF POLYNUCLEOTIDES

The present application is a continuation of U.S. patent application Ser. No. 12/036,048, filed Feb. 22, 2008, now abandoned which is incorporated by reference herein.

BACKGROUND

The incidence of antibiotic resistant bacteria has dramatically increased over the past decade. If not diagnosed and treated appropriately, these human pathogens can cause a range of life-threatening illnesses including septicemia and toxic shock syndrome. Early treatment of these infections has been associated with improved outcomes in patients. Clinical outcome studies have shown that reducing the time to diagnosis decreases the patient's length of stay and morbidity and mortality, leading to significant cost savings for the hospital. Standard microbiological methods in practice today require 24-72 hours to identify the causative pathogen in an infection. Therefore, there is an increasing need for rapid, easy-to-perform tests to identify antibiotic-resistant pathogens.

SUMMARY

The present invention provides systems and methods for amplifying and detecting solution-state polynucleotide targets in a single device. In one aspect, a method for detecting a polynucleotide target in a sample includes applying the sample and a reaction medium to a coated solid support comprised of a solid substrate, a cationic layer, and a plurality of target-specific probes attached to the coated solid support. Polynucleotide targets in the sample are then amplified by an isothermal amplification process. Alternatively, the polynucleotide targets are first hybridized to the probes, eluted from the support, and then amplified within the same device or applied to a second coated solid support for amplification by an isothermal amplification process. The amplification process is carried out under conditions suitable for coupled amplification/hybridization in low salt conditions. An additional, optional high salt hybridization step may be included for enhanced hybridization and increased sensitivity of detection.

Biotinylated primers may be utilized in the amplification reaction to facilitate detection of bound polynucleotide targets captured by the probes on the coated solid support. By way of example, anti-biotin/horseradish peroxidase conjugates can be bound to the biotinylated amplification products immobilized on the surface of the coated solid support. The enzyme-catalyzed conversion of a chromogenic substrate, such as tetramethylbenzidine can result in production of precipitable matter on the surface of the coated solid support creating a signal visually detected by the naked eye under visible light conditions.

In another aspect, a method for detecting polynucleotide targets in a sample includes applying the sample and a reaction medium to a coated solid support comprised of silicon substrate, a cationic layer, and a plurality of target-specific probes attached to the cationic layer. Polynucleotide targets in the sample are then amplified by an isothermal amplification process. The amplification process is carried out under conditions suitable for coupled amplification/hybridization in low salt conditions. An additional, optional high salt hybridization step may be included for increased sensitivity. Through the use of appropriate detection reagents, polynucleotide targets captured by the probes may be visually detected as described below.

Certain aspects of the Applicant's invention are predicated on the unexpected discovery that a cationically configured solid support containing immobilized target-specific capture probes can reduce the negative effects of helicase-catalyzed unwinding and release of surface-bound duplexes from the coated solid support during a coupled isothermal amplification/hybridization process.

In another aspect, a method for detecting the presence or absence of a polynucleotide target in a sample includes applying the sample and a reaction medium to a coated solid support including a solid substrate and a plurality of target-specific probes attached to the coated solid support. The sample is subject to conditions and reagents suitable for denaturing polynucleotide targets by an enzymatic process prior to hybridization and detection of enzymatically denatured polynucleotide targets bound to the target-specific probes.

In a particular embodiment, the coated solid support includes a silicon substrate and a cationic layer attached thereto. The coated silicon support does not comprise a coating layer (such as an anti-reflective layer) capable of mediating eye-visible detection of polynucleotides targets by destructive interference. Target-specific probes attached to the cationic layer are then hybridized to polynucleotide targets in the sample, which are then detected using appropriate detection reagents.

In another aspect, the present invention provides a coated silicon biosensor for direct, visual detection of polynucleotide targets deposited on a coated silicon support comprised of a silicon substrate, a cationic layer, and a plurality of target-specific probes attached to the coated silicon support. The coated silicon support can be configured to support visual detection of polynucleotide targets in the sample by a process that is not based on destructive interferences principles, but rather a combination of light scattering and colorimetry. In particular, Applicant has unexpectedly discovered a type of silicon support that can facilitate rapid, visual detection of bound polynucleotide targets under visible light conditions without the use of an antireflective layer conventionally facilitating detection of analytes, including nucleic acids, based on the principles of destructive interference.

In a preferred embodiment, the present invention utilizes a coupled helicase-dependent amplification (HDA)/hybridization system carried out under isothermal, low salt conditions. Amplification reactions are performed with the amplification primers in solution phase in the presence of the probe-containing silicon support or microchip under conditions providing solution-phase amplification/hybridization reaction kinetics. Amplification products are being continually denatured by helicase. As their concentration(s) increase, the denatured polynucleotides can anneal to oligonucleotide primers, re-anneal to complementary strands or anneal to probes immobilized on the surface of a solid support, such as a microchip. At the conclusion of the reaction, the support or chip may be washed, and the presence of the target polynucleotide detected. When used in conjunction with a silicon-based support or microchip according to the present invention, the coupled amplification/hybridization system is capable of supporting direct visual detection of polynucleotide targets under visible light conditions.

From a 10 µL blood sample or nasal swab containing as few as 10 target sequence copies, high concentrations of material can be rapidly amplified ($10^5$ to $10^{10}$ copies of DNA produced depending on the approach). Advantageously, all signal generation steps can be carried out rapidly under isothermal, low salt conditions, generating highly sensitive signals visible to the unaided eye. Depending on the amount of polynucleotide targets in the sample, the entire process from extraction to detection can be completed within 1 hour, requiring just 10 minutes of hands-on time at low cost using one simple coated solid support without expensive or sophisticated instrumentation.

BRIEF DESCRIPTION OF THE DRAWINGS

FIG. 9 depicts oligonucleotide sequences and/or structural modifications used in the primers or probes described in the Examples below.

DETAILED DESCRIPTION

Figure 1:
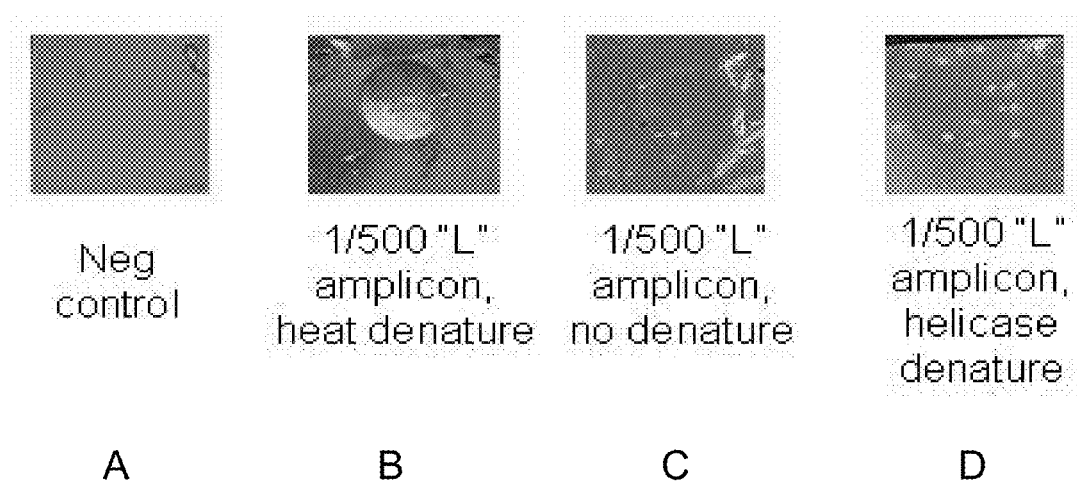
FIG. 1 depicts helicase-mediated denaturation and hybridization of single-stranded polynucleotide targets from aliquots of HDA amplified products diluted 1/5000 in 1× hybridization buffer (high salt) or 1× HDA buffer (low salt).

In order to provide a clear and consistent understanding of the specification and claims, the following definitions are provided.

Units, prefixes, and symbols may be denoted in their SI accepted form. Unless otherwise indicated, nucleic acids are written left to right in 5' to 3' orientation. Numeric ranges recited herein are inclusive of the numbers defining the range and include and are supportive of each integer within the defined range. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. In the case of any amino acid or nucleic sequence discrepancy within the application, the figures control.

As used herein, the phrase "coated solid support" refers to an assay configuration including a solid substrate; one or more coating layers and a plurality of target-specific probes attached to the coated solid support. Exemplary coating layers include but not limited to cationic layers, silane layers, siloxane layers, anti-reflective layers, probe density enhancing materials, attachment layers and the like.

As used herein, the term "surface" generally refers to a covalently-contiguous geometrical domain or a region of a geometrical domain directly contactable by surrounding media and having functional groups supporting chemical interactions between polynucleotides, target-specific probes, and/or surface modified chemical structures through electrostatic interactions, hydrogen bonding, Van der Waals interactions, London interactions, hydrophobic interactions or combinations thereof. In some embodiments of the invention, a zwitter ionic surface may be used to support biomolecular adsorption. A surface of the coated solid support may be fabricated on the solid support or it may be an intrinsic property of the solid support. A nonlimiting example of surface fabrication is aminosilanization wherein cationic functional groups are covalently linked to the solid support.

The term "solid substrate" refers to any material intrinsically having a surface or any material that may be modified to create a surface that can be configured for immobilization of nucleic acid probes. The solid substrate provides a surface that is transferable from solution to solution for detection of polynucleotide targets, and includes but is not limited to slides, sheets, strips, dipsticks, membranes, films, filters, beads, nanoparticles, magnetic particles, microtiter wells, tubes, strings, or any surface that can be configured for immobilization of nucleic acid probes. A solid substrate may be formed from silicon, glass, fiberglass, plastics, such as polycarbonate, polystyrene or polyvinylchloride, complex carbohydrates, such as agarose and Sepharose™, polymeric resins, including those formed from acrylic, such as polyacrylamide, nitrocellulose filters or other membranes, ceramic, latex beads, metals, such as gold, organic and inorganic compounds, or combinations thereof.

The phrase "cationic layer" refers to a cationic layer in the coated solid support, the cationic layer comprising a plurality of cationic functional groups to which are attached target-specific probes or secondary agents to which target-specific probes can be attached.

The term "anti-reflective layer" refers to a thin-film coating that is anti-reflective to specific wavelengths of light so as to create characteristic surface color changes resulting from destructive interference. More particularly, when reflected light from the surface-thin film interface is out of phase with light reflected from the air-thin film interface, specific wavelengths of light are eliminated from the reflecting light by destructive interference so as to create characteristic thin film surface color changes.

The term "functional group" refers to the atom(s) responsible for the characteristic reactions of a compound. For example, the functional group of alcohols is —OH, the functional group of aldehydes is —CHO, the functional group of carboxylic acids is —COON. A given functional group behaves in approximately the same way in all molecules of which it is a part. A single molecule may have a plurality of functional groups. Functional groups may mediate, for example, a noncovalent interaction between a surface and a polynucleotide. Exemplary functional groups may include, but are not limited to biotin, N-hydroxysuccinimide, vinyl-sulfone, metal ion chelates (e.g., $Ni^{2+}$-NTA), glutathione binding group, amino, aldehyde, epoxy, mercapto, maleimide, heparin, methoxy, sulfonate, silane, azide, acrylate, aldehyde, isocyanate, phosphonate, and epoxy.

The term "nucleic acid" refers to a polydeoxyribonucleotide (DNA or an analog thereof) or polyribonucleotide (RNA or an analog thereof) made up of at least two, and preferably ten or more bases linked by a backbone structure. In DNA, the common bases are adenine (A), guanine (G), thymine (T) and cytosine (C), whereas in RNA, the common bases are A, G, C and uracil (U, in place of T), although nucleic acids may include base analogs (e.g., inosine) and abasic positions (i.e., a phosphodiester backbone that lacks a nucleotide at one or more positions, U.S. Pat. No. 5,585,481). Exemplary nucleic acids include single-stranded (ss), double-stranded (ds), or triple-stranded polynucleotides or oligonucleotides of DNA and RNA.

The term "polynucleotide" refers to nucleic acids containing more than 10 nucleotides.

As used herein, the term "oligonucleotide" refers to a single stranded nucleic acid containing between about 15 to about 100 nucleotides.

The term "nucleic acid backbone" refers to nucleic acids groups or linkages, including but not limited to sugar-phosphodiester linkages, 2'-O-methyl linkages, guanidine linkers in DNA ("DNG"), S-methylthiourea linkers, methylphosphonate linkages, phosphoramidate linkages, amide backbone modifications as in polyamide or peptide nucleic acids (PNA), phosphorothioate linkages, phosphonic ester nucleic acid linkages, pyranosyl oligonucleotide linkages, bicyclo- and tricyclo-nucleic acid linkages, formacetal and 3'-thioformacetal linkages, morpholino linkages, or other modifications of the natural phosphodiester internucleoside bond, or combinations of such linkages in a single backbone. A nucleic acid backbone may include a mixture of linkages in the same nucleic acid (e.g., sugar-phosphodiester and 2'-O-methyl linkages) or may have all of one type of linkages (e.g., all 2'-O-methyl or all amide modification linkages).

The term "sample" refers to any biological sample source containing or suspected of possibly containing a polynucleotide target or polynucleotide target sequence. The test sample can be derived from any biological source, such as for example, blood, bronchial alveolar lavage, saliva, throat swabs, ocular lens fluid, cerebral spinal fluid, sweat, sputa, urine, milk, ascites fluid, mucous, synovial fluid, peritoneal fluid, amniotic fluid, tissues, fermentation broths, cell cultures, chemical reaction mixtures and the like. The test sample can be used (i) as directly obtained from a sample source or (ii) following a pre-treatment to modify the character of the sample. Thus, the test sample can be pre-treated prior to use by, for example, preparing plasma from blood, disrupting cells, preparing liquids from solid materials, diluting viscous fluids, filtering liquids, distilling liquids, concentrating liquids, inactivating interfering components, adding reagents, purifying nucleic acids, and the like.

The terms "polynucleotide target", "target sequence", and "target nucleic acid" are used interchangeably and refer to a nucleic acid in a test sample having a sequence of nucleotide bases to which another sequence, such as target-specific probe binds via standard complementary base pairing. The polynucleotide target is directed to a nucleic acid sequence that can be detected, amplified, or both amplified and detected. The polynucleotide target is generally provided in a solution state, which is then hybridized to a target-specific probe. Polynucleotide targets of the invention may be single or double stranded and may comprise DNA, RNA, as well as combinations or derivatives thereof. The target sequence may be a relatively small part of a larger nucleic acid, such as a specific subsequence contained in a genomic DNA or messenger RNA (mRNA). Those skilled in the art will appreciate that a target nucleic acid may exist in different forms, i.e., single-stranded, double-stranded, triple-stranded, or mixtures thereof, such as in a partially double-stranded hairpin structure or partially double-stranded duplex structure, and will further appreciate that a target sequence may be present on any strand (+ or −) of the structure. For simplicity, a target nucleic acid may be described as all or part of a single strand, but this is not meant to limit the meaning of a target to one or a particular nucleic acid strand. It is well known in the art that a multi-stranded nucleic acid is readily converted to its single-strand components by using standard methods, such as by heating a nucleic acid above its melting temperature (Tm) and/or by using chemical denaturants.

The term "target-specific probe" refers to a polynucleotide bound to a surface that binds specifically to a polynucleotide target sequence and which binding is capable of producing, directly or indirectly, a detectable signal to indicate the presence of the polynucleotide target sequence. Preferably, the target-specific probe is a single stranded oligonucleotide having a length between about 12 nucleotides to about 60 nucleotides. The target-specific probe can be linked to a label in the detection step subsequent to hybridization. Labeled target-specific probes may include a linkers and/or a labels thereto (see e.g., U.S. Pat. Nos. 5,185,439, 5,283,174, 5,585,481 and 5,639,604).

The term "blocked" refers to a functional group in (in a polynucleotide, polypeptide or non-polymeric agent) that is chemically modified or derivatized to render the functional group chemically inert or to reduce or eliminate enzymatic recognition as a result of the modification or derivatization. By way of example, a target-specific probe end may be "blocked" (by e.g., a "blocking group") by reaction with or inclusion of a chemical group and/or structural element rendering the probe less suitable for recognition (or reaction) by an enzyme, such as helicase or DNA polymerase, thereby preventing or substantially reducing e.g., the enzyme from binding at, or near the blocked end, or catalyzing an enzymatic reaction at or near the blocked end. A "blocked probe" or "blocked oliognucleotide probe" may be created by structurally modifying an existing oligonucleotide or by pre-engineering a suitable modification or structural element into the original design of, for example, a commercially obtainable oligonucleotide probe. Free amino groups in cationic layers of the present invention may be similarly "blocked" to provide a desirable level of charge density/reactivity on a coated solid support surface.

The term "modified probe", "modified target-specific probe", and "modified oligonucleotide" refers to a single stranded nucleic acid having an unconventional structure, including at least one nucleic acid structural element not found in human genomic DNA. Generally, this refers to a purposeful variant from classical ribo- and deoxyribonucleotides adenine, thymine, guanine, cytosine, or uracil residues linked by phosphodiester bonds. The non-natural structural element may be added to a conventional oligonucleotide or it may be included in the design of the oligonucleotide during its synthesis. When used in this context herein, the term will generally mean: (1) a variant of the classical nucleotides leading to a higher binding efficiency when a target-specific probe is hybridized to a polynucleotide target as compared to an otherwise identical target-specific probe containing the classical nucleotides; and/or (2) a variant of the classical nucleotides producing a substrate with structural features conferring a reduction or elimination in the recognition by an isothermal amplification enzyme of the target-specific probe bound to the polynucleotide target or conferring a reduction or elimination in enzymatic denaturation of the probe bound to the polynucleotide target (as compared to an otherwise identical target-specific probe containing the classical nucleotides).

The term "primer" refers to a single stranded nucleic acid capable of binding to a single stranded region on a polynucleotide target to facilitate polymerase dependent replication and/or amplification of the polynucleotide target.

The term "polymer" refers to a chain of molecules consisting of structural units and repeating units connected by a covalent chemical bond.

The term "silane" or "silanizing reagent" refers to a compound or reagent containing a silicon atom with or without a polymeric chain of repeating subunits. Exemplary silanes include but are not limited to organosilanes, aminosilanes, vinylsilanes, epoxysilanes, methacrylsilanes, sulfursilanes, alkylsilanes, polyalkylsilanes, (alkyl)alkoxysilanes, aminoalkylsilanes, (aminoalkyl)alkoxysilanes (such as (3-aminopropyl)triethoxysilane), and the like.

The term "siloxane" refers to a polymeric compound containing a silicon-oxygen-silicon (Si—O—Si) molecular unit.

As applied to polynucleotides, the term "amplification" refers to refers to any known in vitro procedure for producing multiple copies of a polynucleotide target fragment (i.e. "amplicons") in a linear or exponential fashion with temperature cycling (e.g., polymerase chain reaction, PCR) or without temperature cycling (e.g., isothermal amplication).

The term "isothermal amplification" refers to an amplification process that does not require temperature cycling between the polymerization and nucleic acid denaturation steps. Accordingly, the polymerization and amplification steps in an isothermal amplification process can be carried out at substantially constant temperature conditions. Isothermal temperatures for isothermal amplification reactions are generally below the melting temperature (Tm, the temperature at which half of the potentially double-stranded molecules in a mixture are in a single-stranded, denatured state) of the predominant reaction product, generally 90° C. or below, and usually between about 37° C. to about 75° C.

Although the polymerization reaction may occur in isothermal conditions, an isothermal process may optionally include a pre-amplification heat denaturation step to generate a single-stranded target nucleic acid to be used in the isothermal amplification step.

The term "isothermal amplification enzyme" refers to an enzyme associated with an amplification process, including but not limited to polymerases, enzymatic denaturation enzymes, such as helicases, and denaturation accessory enyzmes, including single stranded binding proteins and the like. An isothermal amplification enzyme may be thermophilic or mesophilic in nature.

The terms "helicase-dependent amplification" and "HDA" are used interchangeably to describe an in vitro reaction process for amplifying nucleic acids that uses a helicase preparation for unwinding a double stranded nucleic acid to generate templates for primer hybridization and subsequent primer-extension via one or more polymerase enzyme(s). HDA utilizes two oligonucleotide primers, a first primer hybridizing to a complementary sequence in the sense strand of a polynucleotide target sequence and a second primer hybridizing to a complementary sequence in the anti-sense strand of a polynucleotide target sequence, whereby the two primers define the outer boundaries of the amplified polynucleotide target. The HDA reaction constitutes a general method for helicase-dependent nucleic acid amplification.

The terms "hybridization" and "hybridize" are used interchangeably to refer to the binding of a primer or target-specific probe to a single stranded region of the polynucleotide target under conditions in which primer or probe binds specifically to its complementary sequence in the polynucleotide target, but not other polynucleotide regions. The specificity of hybridization may be influenced by the length of the oligonucleotide primer, the temperature in which the hybridization reaction is performed, the ionic strength, and the pH.

The terms "complementary" or "complementarity of" are used in the context of nucleic acids to mean that a nucleotide sequence in one nucleic acid strand capable of hydrogen bonding to another sequence on an opposing nucleic acid strand due to the orientation of the functional groups. The complementary bases typically are, in DNA, A with T and C with G, and, in RNA, C with G, and U with A. "Substantially complementary" means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations known to those skilled in the art to predict the Tm of hybridized strands, or by empirical determination of Tm by using routine methods. Tm refers to the temperature at which a population of hybridization complexes formed between two nucleic acid strands are 50% denatured. At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41(% G+C), although other Tm computations are known in the art which take into account other nucleic acid structural characteristics.

The phrase "conditions suitable for hybridization" refers to the cumulative environmental conditions sufficient to facilitate the specific binding of a first nucleic acid strand to a second nucleic acid strand by complementary strand interactions and hydrogen bonding so as to result in a stable hybridization complex or hybrid. Such conditions include the chemical components and their concentrations (e.g., salts, chelating agents, formamide) of an aqueous or organic solution containing the nucleic acids, and the temperature of the mixture. As is known to those skilled in the art, other well known factors, such as the length of incubation time or reaction chamber dimensions may contribute to the environment.

The terms "high salt" or "high salt conditions" are used herein with reference herein to hybridization conditions having a monovalent cation concentration greater than about 0.5 M.

The terms "low salt" or "low salt conditions" are used herein with reference to hybridization conditions in which the monovalent cation concentration between about 10 mM to about 100 mM, preferably between about 25 mM to about 75 mM.

The terms "melting", "unwinding" or "denaturing" refer to separating all or part of two complementary strands of a nucleic acid duplex.

The term "helicase" refers to an enzyme necessary for enzymatically unwinding or denaturing a nucleic acid alone or in combination with at least one helicase accessory protein.

The term "helicase accessory protein" refers to an additional protein that may be necessary for helicase activity or for stimulating helicase activity. Helicase accessory proteins include single strand DNA binding proteins (SSBs), which may be necessary for unwinding nucleic acids when using mesophilic helicases. *E. coli* MutL protein is an exemplary accessory protein for enhancing UvrD helicase melting activity.

The term "helicase preparation" refers to a mixture of helicase(s) and/or helicase accessory proteins necessary and sufficient for enzymatically unwinding or denaturing a nucleic acid. Where a thermostable helicase is utilized in a helicase preparation, the presence of a single stranded binding protein may be optional. A helicase preparation, when combined with a DNA polymerase, a nucleic acid template, deoxynucleotide triphosphates, and primers is generally capable of achieving isothermal nucleic acid amplification in vitro.

The terms "attached" and "linked" are used interchangeably to refer to any chemical connection between two components or compounds, including both direct and indirect chemical connections. The connection can be covalent or non-covalent in nature. Examples of non-covalent attachments include, but are not limited to, electrostatic interactions, ionic interactions, hydrogen bonding, Van Der Waals interactions, dipole-dipole interactions, and hydrophobic interactions.

The term "label" refers to a molecular moiety, compound or conjugate that is directly or indirectly joined to a target-specific probe or polynucleotide target for detection (e.g., an amplified polynucleotide), the label containing a physical or chemical characteristic capable of eliciting a detectable and/or measurable signal indicative of duplex formation between a target-specific probe and a complementary polynucleotide target, including but not limited to enzyme-catalyzed signals and the like. Direct labeling can occur through bonds or interactions that link the label to the polynucleotide (e.g., covalent bonds or non-covalent interactions), whereas indirect labeling can occur through use a "linker" or bridging moiety, such as an oligonucleotide or antibody, which may be further directly or indirectly labeled. Exemplary labels may include but are not limited to chromophores; optically detectable dyes, particles, or compounds, including colorimetric, luminescent, fluorescent, bioluminescent, chemiluminescent, and phosphorescent compounds; antibodies; haptenic or antigenic compounds used in combination with a suitably labeled antibody; specific ligands or binding pair members containing a ligand recognition site, such as such as biotin or avidin; enzymes; enzyme cofactors or substrates; complementary nucleotide sequences; enzymes; enzyme cofactors or substrates; radioisotopes; and the like. Bridging moieties may further be included to amplify a detectable signal. In addition, the label may include a variety of different reactive groups or chemical functionalities suitable for linkage to a variety of biomolecule agents.

It will be understood that directly detectable labels may require additional components such as, for example, substrates, triggering reagents, light, and the like to enable detection of the label. When indirectly detectable labels are used, they are typically used in combination with a "conjugate". A conjugate is typically a specific binding member which has been attached or coupled to a directly detectable label. Coupling chemistries for synthesizing a conjugate are well known in the art and can include, for example, any chemical means and/or physical means that does not destroy the specific binding property of the specific binding member or the detectable property of the label.

The term "signal" refers to a property or characteristic of a detectable label that permits it to be visually or instrumentally detected and/or distinguished. Exemplary signals include but are not limited to chromogenic signals, fluorescent signals, chemiluminescent signals, radioactive signals, and the like.

The phrase "lower limit of detection" (or "LLOD") refers to the lowest concentration of target that can be visually detected in an assay using conventional laboratory equipment.

The present invention provides systems and methods for amplifying and/or detecting solution-state polynucleotide targets. In one aspect, a method for coupled amplification/hybridization/detection of polynucleotide target(s) in a sample includes applying the sample and a reaction medium to a coated solid support comprised of solid support, a cationic layer, and a plurality of target-specific probes attached to the coated solid support. Polynucleotide targets in the sample may be amplified by an isothermal amplification process and hybridized to the target-specific probes under low salt conditions.

Advantageously, the present invention provides coated solid supports and their use in methods for rapid, point-of-care amplification detection of polynucleotide targets bound to the coated solid supports of the present invention. Applicant has unexpectedly discovered a method for amplifying and rapidly detecting a polynucleotide target in a coupled isothermal amplification/hybridization/detection process. Applicant has determined that a cationically configured solid support containing immobilized target-specific capture probes can reduce the negative effects of unwinding and release of surface-bound duplexes from the coated solid support during a coupled isothermal amplification/hybridization process, which might otherwise reduce detection of captured duplexes, particularly under low salt conditions. The negative effects of unwinding and release of duplexes during the coupled isothermal amplification/hybridization process may be also reduced using target-specific capture probes modified or incorporated with a structural element to reduce or eliminate recognition by an isothermal amplification enzyme (such as a helicase) when bound to a polynucleotide target.

Further, the coupled amplification/hybridization/detection system of the present invention can be practiced without requiring separate or extra steps directed to denaturation or annealing of amplicon materials to surface-immobilized single-stranded DNA capture probes.

The coated probe-containing supports of the present invention provide more optimal isothermal amplification/hybridization reaction kinetics. In one aspect, an isothermal amplification reaction is performed in solution phase onto the coated, probe-containing solid support using suitable amplification enzymes, accessory products, and target-specific primers. As the amplified polynucleotide target concentration(s) increase, the polynucleotide targets anneal to oligonucleotide primers, re-anneal to complementary strands, or anneal to probes immobilized on the surface of a solid support, such as a microchip. Target-specific probes may be further modified or incorporated with a structural element to reduce or eliminate recognition by an isothermal amplification enzyme (such as a helicase) when bound to a polynucleotide target. In a preferred embodiment, the amplification products are being continually denatured by helicase in a helicase-dependent amplification reaction under conditions supporting hybridization of single stranded reaction products to a coated solid support in the form of a biosensor chip. At the conclusion of the amplification/hybridization reactions, the support or chip may be washed, and the presence of the polynucleotide target detected.

I. Material Components of the Present Invention

1. Sample and Sample Processing

A sample for use in the present method includes any nucleic acid source containing or potentially containing a polynucleotide target for detection. As such, the sample may include a polynucleotide preparation or extract from any nucleic acid-containing source, including animal cells, microbial cells, such as bacteria and fungi, viruses, or combinations therefrom. Nucleic acids may be extracted from any polynucleotide source material using conventional extraction methodologies known to those of skill in the art, including clinical samples from blood (e.g., 10 µl) or nasal swabs. A nucleic acid extract may be diluted into a reaction buffer for direct amplification. In other embodiments, the sample may include reaction products from an isothermal nucleic acid amplification process or conventional nucleic acid amplification process, such as polymerase chain reaction (PCR).

2. Coated Solid Support

In one embodiment, a coated solid support for polynucleotide target detection includes a solid substrate, a cationic layer, and a plurality of target-specific probes attached to the coated solid support. In another embodiment, a coated solid support for polynucleotide target detection includes a plurality of target-specific probes attached to the coated solid support.

In another embodiment, a coated solid support for polynucleotide target detection includes a silicon-based biosensor for visual detection of a polynucleotide target in a sample. The silicon-based biosensor includes a coated silicon support comprised of a silicon substrate, a cationic layer, and a plurality of target-specific probes attached to the coated silicon support, whereby the coated silicon support is configured to support visual detection of polynucleotide targets in the sample and does not comprise a coating layer capable of mediating visual detection of polynucleotide targets by destructive interference. In a particular embodiment, the coated silicon support does not comprise an antireflective layer used in thin film biosensors.

2.1. Solid Substrate

A solid substrate according to the present invention can be any material intrinsically having a surface or any material that can be modified to create a surface to which a single-stranded nucleic acid may be attached, either covalently or noncovalently. A solid substrate may be formed from silicon, glass, plastic, polypropylene, ceramic, metallic, organic, inorganic materials or combinations thereof. A solid support may be in the form of a slide, microchip, microarray, microtiter plate, dipstick, sheet, membrane filter, film, bead, or any other suitable support forms known in the art.

The solid substrate may be porous or nonporous. Exemplary nonporous substrates include but are not limited to materials commonly used for construction of nucleic acid microarrays, such as glass slides, surface-derivatized glass slides, silicon wafers, or any of a variety of laboratory-grade plastics. Plastic substrate materials may polymethylacrylic, polyethylene, polypropylene, polyacrylate, polymethylmethacrylate, polyvinylchloride, polytetrafluoroethylene, polystyrene, polycarbonate, polyacetal, polysulfone, cellulose acetate, cellulose nitrate, nitrocellulose, and mixtures thereof.

Exemplary porous substrates include bibulous or nonbibulous membrane filters. Filters for nucleic acid attachment and detection are well known in the molecular biology, and include, for example, filters made from nitrocellulose, nylon, or positively-charged derivatized nylon.

In one embodiment, the solid substrate is in the form of silicon wafer or chip. In a particular embodiment, a silicon wafer for use in the present invention includes an un-polished "rough side" surface used for application of cationic layers and/or probes. A rough side silicon surface may be provided by use of a silicon wafer having a polished side and a rough, un-polished side. In one embodiment, the surface of the rough, un-polished side may have a roughness characterized by a peak-to-valley range from about 1 µM to about 10 µM, from about 1 µM to about 5 µM, or from about 0.5 µM to about 2 µM. The roughness of the surface may be governed or modulated by the time of exposure to a caustic bath (e.g., concentrated NaOH, 90° C.). In a particularly embodiment, the rough un-polished silicon surface is subjected to the caustic bath for about 15 seconds.

Applicants have unexpectedly found that the rough side surface of a silicon wafer can be employed without further polishing to provide a visual detection medium without the need for further polishing or thin film coatings for destructive interference-based visual detection. While not wishing to be bound by theory, it is believed that the rough side silicon surface for use in the present invention can support visual detection of polynucleotide targets by a process that is not based on destructive interferences principles, but rather a combination of light scattering and colorimetry.

In alternative embodiments, a thin film coated solid support (or biosensor) may be utilized in which a polished side of a silicon wafer is coated with an antireflective layer to provide a medium for visual detection of target polynucleotides by destructive interference. The antireflective layer may be formed as a coating of silicon nitride as previously described (Jenison et al., Expert Rev. Molec. Diagn., 2006). An additional attachment layer comprised of T-structure polydimethylsiloxane may be formed thereover to facilitate conjugation to the target-specific probes. Exemplary thin film biosensors, including attachment layers for use in a thin-film biosensor for use in the methods of the present invention are described in U.S. Pat. No. 5,955,377 and U.S. patent application Ser. No. 11/761,782, filed Jun. 12, 2007, the disclosures of which are incorporated by reference herein.

Solid substrates for use in the present invention may be molded into any of a variety of shapes and forms. Examples of such shapes and forms include, but are not limited to, sheets, films, slides, gels, foams, filaments, threads, membranes, beads, plates, and the like. Substrates may be fabricated in the form of a planar device having discrete isolated areas in the form of wells, troughs, pedestals, hydrophobic or hydrophilic patches, die-cut adhesive reservoirs or other physical barriers to fluid flow. Examples of such substrates include, but are not limited to, slides, microplates, sheets, films, dipsticks, and the like. Because the devices of the present invention are particularly useful in the preparation of polynucleotide arrays for detection of polynucleotide targets, a cationic layer is preferably fabricated on a device having at least one flat planar surface, such as a slide.

The size of the coated solid support may vary, depending on the final use of the immobilized polynucleotide targets. Those skilled in the art will appreciate that arrays of polynucleotides immobilized on miniaturized solid substrates have been under development for many years. These solid substrates can be measured in terms of $mm^2$ planar surface area and can have numerous different immobilized polynucleotide targets, each attached to a different site-specific location on the miniaturized solid support. Solid substrates in the form of slides or dipsticks are also within the scope of the present invention. As known in the art, dipsticks typically are rectangular in shape with each side measuring a few centimeters.

In a particular embodiment, the solid substrates may include a probe density enhancing material in the form a bead or pellet containing a coated cationic surface. Beads can provide a means for increasing probe density on the coated solid support. A bead may constitute a solid substrate according to the present invention or it may additionally constitute a probe density enhancing material for linkage to another solid substrates or solid substrates coating. The beads can provide a variety of surface chemistries or functionalities (e.g., amine, carboxyl, hydroxy etc.) suitable for rendering the bead cationic by e.g., amination, or by direct or indirect linkage to cationic polymer according to the present invention.

Suitable bead compositions include those used in peptide, nucleic acid and organic moiety synthesis, and include, for example, plastics, such as polystyrene, methylstyrene, acrylic polymers, ceramics, glass, polymeric materials, such as cross-linked dextrans, cellulose, nylon, and latex, paramagnetic materials, titanium dioxide, latex. The beads may encompass any type of solid or hollow sphere, ball, bearing, cylinder, or other solid configuration, which may be porous or non-porous in nature. The use of porous beads can increase the surface area of the bead available for nucleic acid detection. Bead sizes generally range from about 100 nm to about 5 mm, preferably from about 0.2 µm to about 200 µm, more preferably from about 0.5 µm to about 5 µm. Methods for attaching target-specific probes to bead surfaces are described in e.g., U.S. Pat. No. 5,514,785, the disclosures of which are incorporated by reference herein.

A surface or layer on the solid support may be blocked or aged to reduce surface passivation (or non-specific binding) of reaction components so as to interfere with amplification and/or detection of polynucleotides bound to the probes. For example, easily accessible surface amines may be blocked by treatment with NHS-acetate or acetic anhydride. In addition, solid supports, including silicon substrates may be aged (for e.g., 3-12 months) to reduce surface passivation of reaction components thereto.

2.2. Cationic Layer.

Applicants have unexpectedly discovered that a cationic layer can be used in conjunction with probes immobilized onto a coated solid support to reduce the release of and/or increase the detection of captured target sequences on the coated support surface, thereby reducing the potentially negative effects of helicase-catalyzed unwinding and release of bound duplexes from the coated support surface. Moreover, contrary to conventional expectations, Applicants have further discovered that use of a cationic layer coating according to the present invention can actually stabilize the binding and resultant detection of bound polynucleotide duplexes on the surface of the coated solid support under low salt conditions to a greater extent than in high salt conditions typically used in facilitating hybridization.

In one embodiment the cationic layer is configured so that a proportion of the cationic functional groups in the cationic layer retain their cationic functionality following attachment to target-specific probes or secondary agents promoting attachment to the target-specific probes. In one aspect, between about 0.1 to about 10% of the cationic functional groups are retained in the coated solid support following attachment of target-specific probes thereto. In another aspect, between about 0.5 to about 3% of the cationic functional groups are retained in the coated solid support following attachment of target-specific probes thereto.

In one embodiment, the cationic layer is formed from a cationic polymer. Exemplary cationic polymers include polylysine, poly(lys-phe), poly(lys-tyr), poly(lys-trp), poly (arg-trp), and poly(arg-pro-tyr). Preferably, the cationic polymer substantially covers at least a portion of the solid support.

The formation and/or incorporation of cationic layers onto silicon surfaces can be especially facilitated using silane chemistry-based methodologies and compounds well known to those of skill in the art, including use of silane-modified polymers, polysilanes, silazanes, polysilazanes, T-resins, and polyalkosiloxane-polysilicates.

In one embodiment, the cationic layer may be formed from polymeric or non-polymeric substances derivatized to form a cationic layer. In one embodiment, the cationic layer may be created by introducing amine groups on the surface of the solid support. The amine groups may be introduced by cationic silanes, cationic siloxanes, or cationic derivatives thereof, or they may be added via a cationic polymer, for example, onto a coating layer composed of various silanes, siloxanes, or derivatives thereof. By way of example, a coating layer may be comprised of non-aminated coatings, including hydrophobic coatings of polypeptides, silanes, or siloxanes. Aminated layers may then be created thereon through the use of various polycations, such as poly (lys-phe). Such an approach can serve to increase the density of amines and create stable, multilayer coatings.

Exemplary silanes include aminopropyltrimethoxysilane, glycidoxypropyltrimethoxysilane, and aminopropyltriethoxysilane. Exemplary siloxanes include amino-functional organopolylsiloxanes, and amino-functional siloxane alkoxylates. U.S. Pat. No. 6,013,789 describes methods for introducing amine groups onto a polypropylene surface, the relevant content of which is incorporated by reference herein.

A cationic polymer, cationic probe density enhancing material, or aminated surface of the coated support may be chemically derivatized to facilitate linkage to a solid support or to a target-specific capture probe. For example, amino groups may be aldehyde-modified, hydrazide-modified, or sulfhydryl-modified to facilitate chemical conjugation to a suitably modified capture probe. Any crosslinking agent suitable for chemically linking or conjugating functional groups, particularly amino groups in the cationic layer to either the solid support and/or the target-specific capture probes may be used, including but not limited to heterobifunctional NHS esters such as SFB, SHNH, SIAB, and NHS.

A solid support may be chemically modified to form a cationic layer thereover. In particular, solid supports may be modified by introducing a functionality selected from a group consisting of: amino, carboxyl, thiol, and their derivatives. Amino groups may be introduced onto the surface of a solid support by any conventional method known to those of skill in the art, including the use of plasma discharge in an ammonia- or organic-amine-containing gas. The "plasma" is most preferably an ionized gas, which gains sufficient ionization energy from an electromagnetic field. Preferably, the ionization energy is applied by a radio-frequency plasma discharge, a microwave frequency plasma discharge, or a corona discharge. In a particularly preferred embodiment of the invention, the amine is derived from an ammonia gas and the elevated energy state is achieved via radio-frequency plasma discharge.

2.3. Additional Coating Layers.

Additional layers or coatings may be added over the cationic layer, the solid support, or between the cationic layer and the solid support. The additional layer(s) may be added in addition to a cationic layer or as alternatives to the cationic layers. By way of example, the additional coating(s) may be added to a solid support directly. The cationic layer may be then created on the additional coating layer. The additional coatings may include polypeptides, polysaccharides, and/or silane chemistry-based compound coatings, including silane-modified polymers, polysilanes, silazanes, polysilazanes, T-resins, and polyalkosiloxane-polysilicates.

Additional coating layers that may be included in the coated solid support of the present invention include thin-film anti-reflective layers, attachment layers, and probe density enhancing materials.

For example, a coated solid support may further include a thin film anti-reflective layer over the solid support. A thin film anti-reflective layer is anti-reflective to specific wavelengths of light so as to create characteristic surface color changes resulting from destructive interference. More particularly, when reflected light from the surface-thin film interface is out of phase with light reflected from the air-thin film interface, specific wavelengths of light are eliminated from the reflecting light by destructive interference so as to create characteristic thin film surface color changes. In one embodiment, the anti-reflective layer of silicon nitride is deposited by plasma-enhanced chemical deposition. Anti-reflective layers may be deposited on a variety of different supports. Methods and supports for depositing thin film anti-reflective layers in accordance with the present invention are described in U.S. patent application Ser. No. 11/761,782, filed Jun. 12, 2007, the disclosures of which are incorporated by reference herein in their entirety.

An attachment layer may be incorporated into a coated solid support as a layer serving as a chemical bridge connecting the target-specific probes to any layer of the present invention. Preferably, the attachment layer is physically adhered or otherwise chemically attached to a surface of a support or coating layer so as to minimize interference with biochemical processes occurring over the coated supports (e.g., amplification, hybridization, detection) and to provide sufficient durability against subsequent processing steps.

In one embodiment the attachment layer constitutes a coating of suitable coupling agents or cross-linking reagents deposited over a coating layer or solid support surface. The choice of a suitable coupling agent or cross-linking reagent will depend upon the nature of reactive chemical groups and/or the agent chain length which would minimize or avoid intra-unit interference within or between polymers. See "Reagents For Organic Synthesis", L. Fiezer, M. Fiezer, Vol. 1-8, Wiley & Son; "Cross Linking Reagents" (1980 Ed.), Pierce Biochemical Reagent Catalog, Pierce Chemical Co., Rockford III. and references therein, or "Advanced Organic Chemistry" J. March, McGraw Hill (1968).

In one embodiment, probe density enhancing materials are incorporated into the coated solid supports as an attachment layer providing additional or alternative surface chemistries for increasing the probe density on the surface of the cationic layer or the solid support. As such, the probe density enhancing materials are designed for attachment directly or indirectly (e.g., by way of cross-linking agents, etc.) to the target-specific probes of the present invention. Exemplary probe density enhancing materials include latex particles, silica particles, dextran, dextran sulfate, dendrimers, acrylic acid, dextran sulfate, polyvinyl pyrolidone, polyethylene glycol, polyvinyl sulfate, polyvinyl alcohol, polyacrylic acid, poly (acrylamide) acrylic acid copolymer, including chemical and polymeric derivatives thereof.

Upon linking functional groups in any structural component of the present invention, unreacted functional groups may be blocked by chemically modifying or derivatizing the functional group so as to render it chemically inert. By way of example, an end of a target-specific probe may "blocked" (by e.g., a "blocking group" or "capping compound") by reaction with another chemical group rendering a terminus of the probe an unsuitable substrate for an enzyme, such as helicase or DNA polymerase, thereby preventing or substantially reducing the enzyme from binding at, or near the blocked terminus, or catalyzing an enzymatic reaction at or near the blocked terminus. Free amino groups in cationic layers of the present invention may be similarly blocked for improved device performance through optimization of surface charge density/reactivity.

Exemplary blocking agents include, for example, amine-reactive compounds capable of converting free amine groups into amides or imides. By way of example, the blocking agent may be an acetylating reagent. Amine-reactive compounds may include compounds from one or more of the following chemical classes: N-hydroxysuccinimidyl (NHS) esters, imidoesters, aryl halides, acyl halides, isocyanates, isothiocyanates, nitrophenyl esters, carbonyls, carboxylates, and acid anhydrides. Particular amine-reactive compounds may include, for example, any one or more compounds selected from the group consisting of NHS acetate, disuccinimidyl suberate (DSS), succinimidyl-3-(tri-N-butylstannyl)benzoate, methyl N-succinimidyladipate (MSA), mono(latosylamido)mono(succinimidyl)suberate, acetic anhydride, aryl chlorides, acyl chlorides, 2,4-dinitrofluorobenzene (DFNB), sulfonyl halides, aldehydes, 1-ethyl-3-(3-dimethylaminopropyl)-carbodiimide (EDC) based activation chemistries, maleic anhydride, succinic anhydride, acetyl chlorides, benzoyl chlorides, propionyl chlorides, butyryl chlorides, and penylethanoyl chlorides.

Suitable blocking agents may also be selected from non-acetylating agents, such as diazoacetates, imidoesters, carbodimides, maleimides, α-haloacetyls, aryl halides, dicarbonyl compounds, sulfhydryls, and hydrazides. By way of example, specific non-acetylating compounds may be selected from the group consisting of, for example, N-ethyl-maleimide, N-β-maleimidopropionic acid, N-ϵ-maleimidocaproic acid, iodoacetic acid, N-[iodoethyl](trifluoroacetamide), 3,4-difluoronitrobenzene (DFNB), sulfonyl halide, (ammonium 4-chloro-7-sulfobenzo-furazan)-chloride (SBF-chloride), glyoxal, phenyglyoxal, 2,3-butanedione, 1,2-cyclohexanedione, 2-mercaptoethanol, dithiothreitol (DTT) followed by sulfhydryl chemistries, (2,4,6-trinitrobenzene sulfonic acid (TNBSA), and 2-mercaptoethanol. The blocking agent may include or be modified to include a detectable label.

3. Target-Specific Capture Probes

Target-specific capture probes may employ a variety of different polynucleotides or oligonucleotides for detection of polynucleotide target(s). The target-specific capture probes contain sequences complementary to sequences in the polynucleotide target(s), including a first end attached to the coated solid support and an unattached second end.

Target-specific capture probes of the present invention are generally configured as a single stranded polynucleotide attached to the coated solid support, preferably an oligonucleotide between about 12 and 60 nucleotides in length, more preferably 15 to about 40 nucleotides in length.

In one embodiment, the target-specific probes may employ conventional oligonucleotide structures. In another embodiment, the target-specific probe includes a modified oligonucleotide (containing an unconventional nucleic acid structure) capable of forming a duplex structure, whereby the modified oligonucleotide includes a structural feature conferring a reduction or elimination in the recognition of the oligonucleotide by an isothermal amplification enzyme when bound to the polynucleotide target. In a particular embodiment, a target-specific probe includes a modified oligonucleotide incorporating a structural feature conferring a reduction or elimination of enzymatic denaturation when bound to the polynucleotide target Unconventional nucleic acid structures for use in the present invention include oligonucleotides with nonconventional chemical or backbone additions or substitutions, including but not limited to peptide nucleic acids (PNAs), locked nucleic acids (LNAs), morpholino backboned nucleic acids, methylphosphonates, duplex stabilizing stilbene or pyrenyl caps, phosphorothioates, phosphoroamidates, phosphotriesters, and the like. By way of example, the modified oligonucleotides may incorporate or substitute one or more of the naturally occurring nucleotides with an analog; internucleotide modifications incorporating, for example, uncharged linkages (e.g., methyl phosphonates, phosphotriesters, phosphoamidates, carbamates, etc.) or charged linkages (e.g., phosphorothioates, phosphorodithioates, etc.); modifications incorporating intercalators (e.g., acridine, psoralen, etc.), chelators (e.g., metals, radioactive metals, boron, oxidative metals, etc.), or alkylators, and/or modified linkages (e.g., alpha anomeric nucleic acids, etc.) (US 2007/0166741).

In one embodiment, the target-specific probe(s) are internally modified to include at least one neutral charge in its backbone. For example, the capture probe may include a methylphosphonate backbone or peptide nucleic acid (PNA) complementary to the target-specific sequence. These modifications have been found to prevent or reduce helicase-mediated unwinding. The use of uncharged probes may further increase the rate of hybridization to polynucleotide targets in a sample by alleviating the repulsion of negatively-charges nucleic acid strands in classical hybridization (Nielsen et al., 1999, Curr. Issues Mol. Biol., 1:89-104).

PNA oligonucleotides are uncharged nucleic acid analogs for which the phosphodiester backbone has been replaced by a polyamide, which makes PNAs a polymer of 2-aminoethyl-glycine units bound together by an amide linkage. PNAs are synthesized using the same Boc or Fmoc chemistry as are use in standard peptide synthesis. Bases (adenine, guanine, cytosine and thymine) are linked to the backbone by a methylene carboxyl linkage. Thus, PNAs are acyclic, achiral, and neutral. Other properties of PNAs are increased specificity and melting temperature as compared to nucleic acids, capacity to form triple helices, stability at acid pH, non-recognition by cellular enzymes like nucleases, polymerases, etc. (Rey et al., 2000, FASEB J., 14:1041-1060; Nielsen et al., 1999, Curr. Issues Mol. Biol., 1:89-104).

Methylphosphonate-containing oligonucleotides are neutral DNA analogs containing a methyl group in place of one of the non-bonding phosphoryl oxygens. Oligonucleotides with methylphosphonate linkages were among the first reported to inhibit protein synthesis via anti-sense blockade of translation. However, the synthetic process yields chiral molecules that must be separated to yield chirally pure monomers for custom production of oligonucleotides (Reynolds et al., 1996, Nucleic Acids Res., 24:4584-4591).

In one embodiment, the target-specific oligonucleotide probes utilize a backbone of modified sugars joined by phosphodiester internucleotide linkages. The modified sugars may include furanose analogs, including but not limited to 2-deoxyribofuranosides, α-D-arabinofuranosides, α-2'-deoxyribofuranosides, and 2',3'-dideoxy-3'-aminoribofuranosides. In alternative embodiments, the 2-deoxy-β-D-ribofuranose groups may be replaced with other sugars, for example, β-D-ribofuranose. In addition, β-D-ribofuranose may be present wherein the 2-OH of the ribose moiety is alkylated with a $C_{1-6}$ alkyl group (2-(O—$C_{1-6}$ alkyl) ribose) or with a $C_{2-6}$ alkenyl group (2-(O—$C_{2-6}$ alkenyl) ribose), or is replaced by a fluoro group (2-fluororibose).

Related oligomer-forming sugars include those used in "locked nucleic acids" (LNA), which are bicyclic nucleic acids in which a ribonucleoside (including e.g., a furanose ring) is linked between the 2'-oxygen and the 4'-carbon atoms with a methylene unit. LNAs were first described by Wengel and co-workers as a class of conformationally restricted oligonucleotide analogues (Koshkin et al., Tetrahedron, 54:3607-3630 (1998); Singh et al., Chem. Comm., 4:455-456 (1998). Exemplary LNA nucleotides include modified bicyclic monomeric units with a 2'-O-4'-C methylene bridge, such as those described in U.S. Pat. No. 6,268,490, the disclosures of which are incorporated by reference herein.

Oligonucleotides containing α-D-arabinofuranosides can be prepared as described in U.S. Pat. No. 5,177,196. Oligonucleotides containing 2',3'-dideoxy-3'-aminoribofuranosides are described in Chen et al. Nucleic Acids Res. 23:2661-2668 (1995). Synthetic procedures for locked nucleic acids (Singh et al, Chem. Comm., 455-456 (1998); Wengel J., Acc. Chem. Res., 32:301-310 (1998)) and oligonucleotides containing 2'-halogen-2'-deoxyribofuranosides (Palissa et al., Z. Chem. 27:216 (1987)) have also been described.

Duplex stabilizing stilbene or pyrenyl caps include trimethoxystilbene and pyrenylmethylpyrrolindol caps (Glen Research, Sterling, Va.).

Other sugar moieties compatible with hybridization of the oligonucleotide can also be used, and are known to those of skill in the art, including, but not limited to, α-D-arabinofuranosides, α-2'-deoxyribofuranosides or 2',3'-dideoxy-3'-aminoribofuranosides. Oligonucleotides containing α-D-arabinofuranosides can be prepared as described in U.S. Pat. No. 5,177,196. Oligonucleotides containing 2',3'-dideoxy-3'-aminoribofuranosides are described in Chen et al. Nucleic Acids Res. 23:2661-2668 (1995).

Chemically modified oligonucleotides may also include, singly or in any combination, 2'-position sugar modifications, 5-position pyrimidine modifications (e.g., 5-(N-benzylcarboxyamide)-2'-deoxyuridine, 5-(N-isobutylcarboxyamide)-2'-deoxyuridine, 5-(N-[2-(1H-indole-3yl)ethyl]carboxyamide)-2'-deoxyuridine, 5-(N-[1-(3-trimethylammonium) propyl]carboxyamide)-2'-deoxyuridine chloride, 5-(N-napthylcarboxyamide)-2'-deoxyuridine, and 5-(N-[1-(2,3-dihydroxypropyl)]carboxyamide)-2'-deoxyuridine), 8-position purine modifications, modifications at exocyclic amines, substitution of 4-thiouridine, substitution of 5-bromo- or 5-iodo-uracil, methylations, unusual base-pairing combinations, such as the isobases isocytidine and isoguanidine, and the like.

The phosphate backbone in the target-specific probe(s) may employ oligonucleotides containing phosphorothioate linkages or phosphoroamidates (Chen et al., Nucl. Acids Res., 23:2662-2668 (1995)). Combinations of such oligonucleotide linkages are also within the scope of the present invention.

In another embodiment, the 5' or 3' probe end in the target-specific probe may be blocked to reduce or eliminate recognition by an isothermal amplification enzyme, such as a polymerse and/or enzymatic denaturation by an isothermal amplification enzyme, such as a helicase. In one embodiment, at least one of the 5' or 3' probe ends is modified or blocked by capping or by incorporation of a suitable terminus modifier or spacer modifier as further described below (Glen Research, Sterling, Va.). By way of example, an unattached 3'-OH probe end may be modified or blocked to prevent incorporation of the probe into a primer extension product by a polymerase during amplification. This may be achieved by: (i) removing the 3'-OH; (ii) incorporating a nucleotide lacking a 3'-OH, such as dideoxynucleotide; (iii) incorporating cordycepin (3'- deoxyadenosine) and other 3'-bases without a 3'-OH moiety; (iv) incorporating a spacer lacking a 3'-OH, such as C3 propyl spacer; (v) incorporating an amine or phosphate group; or (vi) any other chemical modification rendering the probe inert as a primer for primer extension as known to those of skill in the art. Incorporating a biotin label onto the 3' hydroxyl of the last nucleotide can serve a dual purpose by also acting as a label for subsequent detection or capture of the nucleic acid attached to the label.

In a further aspect, the probe may be modified or designed with other functionalities increasing the utility of the amplification/detection system. In a particular embodiment, the probe includes or is chemically linked to a cleavable linker facilitating the release of hybrid duplexes from the coated solid support for further amplification and/or detection. The design and use of cleavable linkers in oligonucleotide probes is described in U.S. Pat. Nos. 5,380,833, 6,060,246, 6,027,879, and 7,291,471, and U.S. Pat. Appl. No. 2005/0106576, the disclosures of which are incorporated by reference herein. Photocleavable oligonucleotide modifiers, including photocleavable spacer modifiers are commercially available (Glen Research, Sterling, Va.).

In a further aspect, the probe may include or be chemically linked to a terminus modifier or spacer modifier at the 5'-end, 3'-end or both. A terminus modifier or spacer modifier may be incorporated to increase the distance between the capture probe target sequences and the surface of the coated solid support and/or to reduce or eliminate recognition of an isothermal amplification enzyme or enzymatic denaturation by an isothermal amplification enzyme when bound to a polynucleotide target. Exemplary terminus modifiers and spacer modifiers include, for example, a variety of commercially available 5'-amino modifiers, 3-amino modifiers, and chemically derivatized modifiers thereof; spacer phosphoramidates for inserting variable length spacer arms; spacers for introducing abasic sites within an oligonucleotide; and photocleavable spacer modifiers (Glen Research, Sterling, Va.).

The target-specific capture probes may be directly or indirectly attached to any component of the coated solid support, including the solid support, the cationic layer, a probe density enhancing material, or a suitably modified solid support surface. The probe may be covalently or non-covalently attached by its 5' or 3' end to the coated solid support. The probe may be covalently attached through cationic functional groups directly or through functional groups incorporated thereto for purposes of facilitating this attachment. To facilitate attachment to any part of the coated solid support, probes may be modified or designed to include at their 5' or 3' terminal ends a variety of functional groups for enhancing conjugation to other polymer- or nucleic acid-based elements. Exemplary functional groups include amino, hydrazide, aldehyde, and sulfhydryl groups.

A plurality of the same or different target-specific probes may be directly or indirectly attached to the cationic layer or a cation-modified solid support. Either end of the DNA molecule (5' or 3' end) in the target-specific capture probe may be attached to the solid support or to the cationic layer. In addition, as described above, the unattached capture probe ends may be blocked to reduce helicase recognition or primer extensions therefrom.

In one embodiment, the capture probe is attached to a polycationic polymer in the cationic layer. In another embodiment, the capture probe is attached to a cationic silane, cationic siloxane, or cationic derivative in the cationic layer. In a preferred embodiment, the capture probe is linked to a cationic polymer (such as phe-lys) derivatized with an aldehyde functionality.

A coated solid support may include one type of target-specific probe of a single specificity or a plurality of different target-specific probes with multiple specificities for detecting a plurality of different target sequences from one organism, a plurality of different organisms or combinations thereof. The probe(s) may be attached to a discrete area in the solid support as a spot or to a plurality of discrete areas in the form of an array.

II. Methods for Amplifying and Detecting Polynucleotide Targets

1. Amplification/Hybridization Detection System

The coated solid supports of the present invention are configured to allow for isothermal amplification, hybridization and detection on a single detection device. An isothermal amplification process is particularly suited for use in such a device, since it does not require high heat denaturation temperatures for DNA amplification which may be incompatible with the materials used in a coupled amplification/hybridization/detection device.

In one embodiment, a method for amplification/hybridization/detection of polynucleotide target(s) in a sample includes applying the sample and a reaction medium to a coated solid support comprised of a solid substrate, a cationic layer, and a plurality of target-specific probes attached to the coated solid support. In an alternative embodiment, the amplification/hybridization/detection includes a coated solid support comprised of a solid substrate and a plurality of target-specific probes attached to the coated solid support. Polynucleotide targets in the sample are then amplified by an isothermal amplification process and hybridized to the target-specific probes. Upon amplification of nucleic acids in the sample for a period of time sufficient for detection, the polynucleotide targets may be hybridized to the target-specific probes that are attached to the coated solid support.

In one embodiment, a coupled amplification/hybridization/detection system includes an isothermal amplification process utilizing an enzyme, such as helicase, or set of enzymes capable of unwinding the synthesized amplification products. The unwound single stranded amplification products can anneal to amplification primers, re-anneal to complementary strands, or anneal to probes immobilized on the surface of a coated solid support. Polynucleotides may be amplified and hybridized to the coated solid support under low salt conditions or be subjected to an optional high salt hybridization step (for enhanced sensitivity), followed by low salt washes and detection of the bound complexes.

In another embodiment, an uncoupled amplification/hybridization/detection system is employed whereupon completion of the isothermal amplification process, the isothermal amplification products are denatured by heat or a suitable combination of unwinding enzymes to allow for their hybridization to the target-specific probes that are attached to the coated solid support. Inclusion of the terminal denaturation/unwinding step can be applied to any isothermal amplification process carried out on any one of the coated supports of the present invention.

In one aspect, polynucleotide targets in the sample are initially purified by hybridization onto a coated solid support and then transferred to a second coated solid support for the coupled amplification/hybridization/detection process. In this case, polynucleotide targets bound to cleavable, target-specific probes are eluted from a first coated solid support, and then applied to a second coated solid support for amplification by an isothermal amplification process, such as HDA. Following conventional washes to remove non-specifically bound polynucleotides and other polynucleotides or reaction components, cleavable target-specific probes attached to the coated support are cleaved, whereby the cleaved probes, including those hybridized to the polynucleotide targets are subjected to isothermal amplification over a second coated solid support. Amplification products hybridized to the second coated solid support may be directly detected under low salt conditions or optionally subjected to a short (e.g. 15-30 minute) high salt hybridization step (for enhanced sensitivity), followed by low salt washes and detection of the bound complexes. Alternatively, the bound complexes may be subjected to additional cycles of elution, amplification, and/or hybridization prior to detection.

2. Hybridization/Detection System

In one embodiment, a method includes applying a sample and a reaction medium to a coated solid support comprised of a solid support and a plurality of target-specific probes attached to the coated solid support. The coated solid support may further include a cationic layer as described above. Conditions and reagents suitable for denaturing polynucleotide targets in the sample by an enzymatic process are provided, followed by hybridization of the enzymatically denatured polynucleotide targets in the sample to the target-specific probes. In a final step, the presence or absence of polynucleotide targets bound to the probes is detected.

In another embodiment, the hybridization/detection system includes applying a sample and a reaction medium to a coated silicon support comprised of a solid support, a cationic layer, and a plurality of target-specific probes attached to the coated solid support. The coated silicon support does not comprise a coating layer capable of mediating visual detection of polynucleotide targets by destructive interference. In a particular embodiment, the rough side of a silicon support is coated with the cationic layer and the plurality of target-specific probes. Conditions and reagents suitable for hybridizing polynucleotide targets in the sample to the target-specific probes are provided. For example, the polynucleotide targets may be enzymatically denatured prior to the hybridization step as described above. In a final step, the presence or absence of polynucleotide targets bound to the probes is detected. In a particular embodiment, the hybridization and detection steps may be carried out under low salt conditions as described above. As described above, when used in conjunction with a cationic layer, the hybridization and detection steps may be carried out under low salt conditions, and may optionally include a 15-30 minute high salt hybridization step as well.

3. Isothermal Amplification of Polynucleotide Targets

Amplification of polynucleotide targets necessarily requires a suitable polymerase and a means for denaturing or unwinding polynucleotides created during the process of isothermal amplification. In one embodiment, all denaturation and amplification steps are carried out enzymatically under isothermal temperature conditions. In another embodiment, the polynucleotide sample is initially denatured by heat denaturation before the primer annealing step, and then enzymatically denatured during the subsequent amplification/hybridization steps. Alternatively, or in addition, the polynucleotide sample may be amplified in solution phase first and then heat denatured prior to hybridization and detection of amplification products on the coated solid support.

Any isothermal amplification process known to those of skill in the art may be adapted for use in the methods and kits of the present invention. Exemplary isothermal amplification processes and reagents for use in the present invention are incorporated by reference herein with regard to helicase-dependent amplification (HDA) as described in U.S. Pat. No. 7,282,328; strand-displacement amplification (SDA) as described in U.S. Pat. Nos. 5,270,184, 5,422,252, 5,455,166, 5,470,723, 6,087,133, 6,531,302); multiple displacement amplification (MDA) as described in U.S. Pat. No. 6,977,148; recombinase polymerase amplification (RPA) as described in Piepenburg et al., PLoS Biology, 4(7):1115-1121, 2006, U.S. Pat. No. 7,270,981, and U.S. Pat. Appl. No. 2005/0112631; loop-mediated isothermal amplification (LAMP) as described in U.S. Pat. Nos. 6,410,278, 6,743,605, and U.S. Pat. Appl. No. 2007/0218464; rolling circle amplification (RCA) as described in Fire et al., Proc. Natl. Acad. Sci. USA, 92:4641-4645 (2002), Dean et al., Proc. Natl. Acad. Sci. USA, 99:5261-5266 (2002), U.S. Pat. Nos. 5,714,320, 5,854,033, 6,235,502, and 6,344,329; nucleic acid sequence based amplification (NASBA) as described in U.S. Pat. No. 5,130,238; transcription-mediated RNA amplification (TMA) as described in U.S. Pat. Appl. No. 2007/0178470; single primer isothermal amplification (SPIA™ and Ribo-SPIA™, NuGen Technologies, San Carlos, Calif.) as described in U.S. Pat. Nos. 6,251,639, 6,692,918, and 6,946,251 and U.S. Pat. Appl. No. 2007/0212695; and other isothermal amplification methodologies known to those of skill in the art, including those described in U.S. Pat. No. 6,929,915.

An HDA process requires a polymerase preparation for synthesis of amplification products and a helicase preparation to facilitate enzymatic denaturation and annealing of amplification primers to the amplified polynucleotide targets. A suitable helicase preparation includes at least one type of helicase alone or in combination with a helicase accessory product, such as single-stranded binding proteins (SSBs). Preferably, the helicase is a thermostable helicase, which is capable of mediating HDA in the absence of additional accessory products.

The term "helicase" refers to any enzyme capable of enzymatically unwinding or denaturing a nucleic acid alone or in combination with a helicase accessory protein. Helicases can unwind double stranded nucleic acids in the '5 direction or 3' directions. Helicases are found in all organisms and are utilized in enzymatic processes involving nucleic acids, including replication, recombination, repair, transcription, translation and RNA splicing. Any helicase that translocates along DNA or RNA in a 5' to 3' direction or in the opposite 3' to 5' direction may be used in present embodiments of the invention. This includes helicases obtained from prokaryotes, viruses, archaea, and eukaryotes or recombinant forms of naturally occurring enzymes as well as analogues or derivatives having the specified activity. Examples of naturally occurring DNA helicases include *E. coli* helicase I, II, III, & IV, UvrD helicase, Rep helicase, RecQ helicase, PcrA helicase, RecBCD helicase, DnaB helicase, PriA, PcrA, T4 Gp41helicase, T4 Dda helicase, T7 Gp4 helicases, SV40 Large T antigen, herpesvirus helicases, including HSV-1 helicase, yeast RAD, yeast Sgs1 helicase, DEAH_ATP-dependent helicases, RecQ helicase, thermostable UvrD helicases from *T. tengcongensis* and *T. thermophilus*, thermostable DnaB helicase from *T. aquaticus*, MCM helicase, as well as analogs, homologs, thermostable helicases, genetically-modified helicase variants of the above, or any of the helicases disclosed in U.S. Pat. No. 7,282,328, the disclosures of which are incorporated by reference herein.

Under certain circumstances, helicases (especially mesophilic helicases) require or exhibit improved activity in the presence of single-strand binding proteins (SSB), a helicase cofactor known to stabilize single stranded nucleic acids. In these circumstances, the choice of SSB is generally not limited to a specific protein. Examples of single strand binding proteins include T4 gene 32 protein, *E. coli* SSB, T7 gp2.5 SSB, phage phi29 SSB (Kornberg and Baker, supra (1992)) and truncated forms of the aforementioned. Compositions and methods for HDA are described in U.S. Pat. No. 7,282,328, the disclosures of which are expressly incorporated by reference herein.

A variety of different polymerases may be used for amplifying polynucleotide targets. Use of these polymerases may be selected on the basis of processivity and strand displacement activity. Subsequent to melting and hybridization with a primer, the nucleic acid is subjected to a polymerization step. A DNA polymerase is selected if the nucleic acid to be amplified is DNA. When the initial target is RNA, a reverse transcriptase is used first to copy the RNA target into a cDNA molecule and the cDNA is then further amplified in HDA by a selected DNA polymerase. The DNA polymerase acts on the target nucleic acid to extend the primers hybridized to the nucleic acid templates in the presence of four dNTPs to form primer extension products complementary to the nucleotide sequence on the nucleic acid template.

In one embodiment, the DNA polymerase is selected from a group of polymerases lacking 5' to 3' exonuclease activity and which additionally may lack 3'-5' exonuclease activity. Exemplary DNA polymerases include an exonuclease-deficient Klenow fragment of $E.$ $coli$ DNA polymerase I (New England Biolabs, Inc. (Beverly, Mass.)), an exonuclease deficient T7 DNA polymerase (Sequenase; USB, (Cleveland, Ohio)), Klenow fragment of $E.$ $coli$ DNA polymerase I (New England Biolabs, Inc. (Beverly, Mass.)), Large fragment of Bst DNA polymerase (New England Biolabs, Inc. (Beverly, Mass.)), KlenTaq DNA polymerase (AB Peptides, (St Louis, Mo.)), T5 DNA polymerase (U.S. Pat. No. 5,716,819), and Pol III DNA polymerase (U.S. Pat. No. 6,555,349).

DNA polymerases possessing strand-displacement activity, such as the exonuclease-deficient Klenow fragment of $E.$ $coli$ DNA polymerase I, Bst DNA polymerase Large fragment, and Sequenase, are preferred for Helicase-Dependent Amplification. T7 polymerase is a high fidelity polymerase having an error rate of $3.5 \times 10^5$ which is significantly less than Taq polymerase (Keohavong and Thilly, Proc. Natl. Acad. Sci. USA 86, 9253 9257 (1989)). T7 polymerase is not thermostable, however, and therefore is not optimal for use in amplification systems that require thermocycling or that are enhanced at higher temperatures. T7 Sequenase is a preferred polymerase for amplification of DNA by isothermal HDA processes.

4. Hybridization of Polynucleotide Targets

Conditions suitable for promoting formation of hybridization complexes between the target-specific probe and its complementary strand in the polynucleotide target to produce a hybridization complex are well known in the art. As is known to those skilled in the art, the specificity of hybridization may be influenced by the length and composition of the oligonucleotide primer, the temperature in which the hybridization reaction is performed, the ionic strength, and the pH. Suitable conditions may be empirically determined. Hybridization conditions may include the chemical components and their concentrations (e.g., salts, chelating agents, formamide) of an aqueous or organic solution containing the nucleic acids, and the temperature of the mixture. Other well known factors, such as the length of incubation time and physical nature and dimensions of the solid support may contribute to an appropriate environment for hybridization and may be also modified as known to those of skill in the art. Bound complexes may be washed to remove un-hybridized polynucleotides and other reaction components prior to further amplification or detection of polynucleotide targets.

5. Detection of Polynucleotide Targets

Polynucleotide targets bound to complementary target-specific probes on coated solid supports in the above described coupled amplification/detection or hybridization/detection systems may be detected using any suitable detection methodology known to those of skill in the art. Detection may be provided by such characteristics as color change, luminescence, fluorescence, or radioactivity. Typically, the detection of polynucleotide targets is facilitated by complexing to a suitable label or reporter. A suitable label may include any molecular moiety or group having a physical or chemical characteristic capable of producing a response or signal that is directly or indirectly detectable and/or measurable, for example, by catalyzing a reaction that produces an optically detectable signal. The label may be incorporated into the starting materials before or during the completion of any one of the amplification, hybridization, and/or detection steps.

Exemplary labels include but are not limited to chromogenic dyes or substrates facilitating colorimetric detection; luminescent moieties, including fluorescent, bioluminescent, phosphorescent, or chemiluminescent compounds; haptenic or antigenic compounds used in combination with a suitably labeled antibody; specific binding pair members containing a ligand recognition site (e.g., biotin and avidin); enzymes; enzyme substrates, radioisotopes; metal complexes; magnetic particles; radio frequency transmitters, and the like. In addition, the label may include a variety of different reactive groups or chemical functionalities suitable for linkage to a variety of biomolecule agents.

In one embodiment, the label includes an enzyme catalyzing reaction of substrates to produce colored, fluorescent, luminescent, electron dense or radioactive products. More particularly, the label may be linked to bound target polynucleotides to form a chromogenic, precipitable polynucleotide label complex of a size and composition such that light scattered from the complex on illumination with white light can be detected by human eye, preferably without magnification.

Exemplary enzyme labels include peroxidases, such as horseradish peroxidase (HRP), alkaline or acidic phosphatase, galactosidase, glucose oxidase, NADPase, luciferase, carboxypeptidase and the like. In some embodiments, direct visual detection may be enhanced by using an enzyme catalyzing the formation of precipitable, chromophore-containing products producing a visible color change. Colored precipitates can be monitored by e.g., spectrophotometry, flatbed scanning, microscopy, or by the naked eye. Exemplary enzymes catalyzing formation of precipitable, chromophore-containing products include horseradish peroxidase (HRP), alkaline phosphatase, and glucose oxidase.

Enzyme labels may be supplied in the form of enzyme/binding member conjugates or antibody-enzyme conjugates. Exemplary enzyme conjugates include streptavidin/HRP- and anti-biotin antibody/HRP conjugates. Exemplary chromogenic substrates for HRP include 3,3',5,5' tetramethylbenzidine (TMB), 3,3'-diaminobenzidine (DAB), and 3-amino-9-ethyl carbazol (AEC). TMB is a non-precipitating substrate that acts as electron donor for the conversion of hydrogen peroxide into water. TMP is enzymatically converted to a visually detectable colored complex by HRP. Exemplary chromogenic substrates for alkaline phosphatase include BCIP/NBT, Fast Red and AP-Orange. Avidin-linked enzymes and chromogenic substrates are commercially available from, for example, Pierce Chemical Company (Rockville, Ill.) and Sigma (St. Louis, Mo.). Enzymatic labeling and detection are described, for example, in U.S. Pat. No. 4,789,630, the disclosures of which are incorporated by reference herein.

Binding pair members containing a ligand recognition site, such as biotin and avidin, may be incorporated into any of the amplification primers or in the target-specific probes.

Fluorometric detection methods are based on emission of photons or excitons of lesser energy or different wavelength from certain molecules following excitation at a suitable wavelength found in ultraviolet light, for example. There are a variety of fluorescent molecules known to those of skill in the art which can serve as reporters than can be detected and quantified, after excitation at a suitable wavelength, with several apparatuses such as fluorometers, confocal fluorescence scanners, microscopes, etc. Detection of polynucleotide targets may be facilitated by incorporating fluorescent labels or dyes into the amplification primers as known to those of skill in the art.

Chemiluminescent detection relies on enzymes such as alkaline phosphatase or horseradish peroxidase, which can convert a substrate with concomitant emission of light that can be detected by autoradiography (solid phase) or luminometry (liquid phase)

Electrochemical detection is generally performed at the surface of electrodes, whereby oxydo-reduction reactions of reporter molecules yield electrons that can be monitored using a suitable apparatus, such as a potentiostat.

In another embodiment, cationic polymers may be utilized for electrostatic-based detection of polynucleotide targets bound to capture probes in the coated solid supports of the present invention. Cationic polymer-based nucleic acid detection methodologies are typically based on electrostatic interactions between positively charged polymers and negatively charged nucleic acids (Pending patent application PCT/CA02/00485; Ho et. al., 2002, Angew. Chem. Int. Ed., 41:1548-1551; Ho et al., 2002, Polymer Preprints, 43:133-134; Nilsson et al., 2003, Nat. Mater. 2:419-424). These approaches exploit a modification of the optical or electrochemical properties of polymer biosensors upon electrostatic binding to a single- or a double-stranded negatively-charged nucleic acid molecule. These macromolecular interactions are associated with conformational and solubility changes which contribute to signal generation (Ho et. al., 2002, Angew. Chem. Int. Ed., 41:1548-1551). These polymer-based detection technologies do not require any chemical labeling of the probe or of the target and can discriminate between specific and non-specific hybridization of nucleic acids that differ by a single nucleotide acid.

Exemplary cationic "reporter" polymers include various polythiophene derivatives, including water-soluble fluorescent zwitterionic polythiophene derivatives (Nilsson et al., 2003, Nat. Mater. 2:419-424) and water soluble polyfluorene phenylene conjugates (Gaylord et al., 2002, Proc. Natl. Acad. Sci. U.S.A., 99:10954-10957), and poly(3,4-ethylenedioxythiophene) (Krishnamoorthy et al., 2004, Chem. Commun., 2004:820-821). Cationic polymer-based detection methodologies and reagents are further described in U.S. Pat. Appl. Publ. Nos. 2004/0171001 and 2007/0178470, the disclosures of which are incorporated by reference herein.

Detection of polynucleotide labels may be facilitated by the use of an "amplification label," which is a molecule that can amplify the number of detectable labels that can be bound to a polynucleotide target(s). An amplification label may, for example, comprise a polymer that specifically binds to a polynucleotide target and has a plurality of binding sites to which labels can be attached to generate multiple detectable signals relative to one or more bound polynucleotide targets. By way of example, the amplification label may be a polymer having a plurality of amine groups facilitating covalent attachment to a plurality of biotin molecules. The biotin molecules can then be used to generate a detectable signal. Because each biotin molecule generates an independent signal, there are multiple signals generated relative to a bound polynucleotide target to which the polymer binds, thereby amplifying the corresponding signal thereto. Amplification labels and associated detection reagents are disclosed in U.S. Provisional Pat. Appl. No. 60/990,755, filed Nov. 28, 2007, the disclosures of which are incorporated by reference herein.

III. Kits for Amplification and/or Detection of Polynucleotide Targets

In one embodiment, a kit for isothermal amplification includes an above-described coated solid support and one or more enzymes collectively sufficient for an isothermal amplification process. In a particular embodiment, the coated solid support includes a cationic layer. In another embodiment, the coated solid support is attached to at least one target-specific probes formed from an oligonucleotide modified or incorporated with a structural element reducing or eliminate recognition by an isothermal amplification enzyme when bound to a polynucleotide target as described above.

When supplied as a kit, any of the various components or reagents may be packaged in separate containers and admixed prior to use with the solid supports of the present invention. Such separate packaging of the components permits long-term storage. Thus, for example, a kit may supply anhydrous amplification enzymes and/or enzyme substrates, and buffers for reconstituting the enzymes and/or enzyme substrates. Any buffers designed to maintain a suitable pH under the reaction conditions of the present invention are contemplated. The anhydrous preparations may be lyophilized, in which water is removed under vacuum, freeze-dried, crystallized, or prepared using any other method removing water so as to preserve the activity of the anhydrous reagents. Excipients may be added to these preparations to stabilize these reagents, such as serum albumins or Prionex. In other embodiments, the reagents may be suspended in an aqueous composition comprising, or example, glycerol or other solvents in which the enzymes and/or other reagents are stable.

The kit may further include cell lysing reagents (including non-ionic detergents (such as from the Triton series), cationic detergents, anionic detergents, zwitterionic detergents, and the like); one or more reaction mediums for hybridization of polynucleotide targets to the probes and for removal of non-specifically bound reaction components; neutralization buffers; wash buffers, and any of the above-described detection reagents or solutions for detection of polynucleotide targets bound to the probes.

The kits may include reagents in separate containers to facilitate the execution of a specific test, such as cell lysis or solution phase amplification. Polynucleotides and primers pairs may be supplied used as internal controls or positive controls with respect to hybridization and/or amplification. The kit may supply a sample gathering component such as a membrane, filter or swab.

The reagents included in the kits can be supplied in containers of any sort such that the life of the different components are preserved, and are not adsorbed or altered by the materials of the container. For example, sealed glass ampules may contain lyophilized enzymes or buffers that have been packaged under a neutral, non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include simple bottles that may be fabricated from similar substances as ampules, and envelopes, that may consist of foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

The kits may be further supplied with a set of instructions for using the contents in a given kit. The instructions may be printed on paper or other substrate, and/or may be supplied as an electronic-readable medium, such as a floppy disc, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as electronic mail. The instructions may instruct the user of the kit in any aspect of the above-described methods, method steps or methodologies relating to the practice of the present invention.

The following Examples are provided to aid in the understanding of the invention and not construed as a limitations thereof

Example 1

Target-Specific Coated Support Preparation

"Rough-side" silicon biosensors employed a silicon wafer having a polished side and an un-polished side, whereby the un-polished "rough" side surface was used for coatings and testing. Thin film biosensors (Inverness Medical-Biostar; Jenison et al., Expert Rev. Molec. Diagn., 2006) employed silicon wafers coated on a polished side with ~475 angstroms of silicon nitride, followed by coating with ~135 angstroms of T-structure aminoalkyl polydimethyl Isiloxane (United Chemical Technologies) as an attachment layer. Surfaces were coated with 5 µg/ml of poly(lys-phe) (Sigma) in 1× PBS pH 6, 2 M NaCl over night at room temperature with rotation. Surfaces were washed with water and then coated with 10 µM SFB (succinimidyl formyl benzoate (Solulink) in 0.1 M Borate pH 8.5) to convert free amino groups to free aldehydes for creating stable hydrazone linkages with hydrazide-modified capture probes. After SFB coating, wafers were extensively washed with water, dried with a stream of nitrogen, and stored in a nitrogen purged dry box. DNA capture probes, modified at the 5'-end with hydrazide linkers, were diluted to 50, 150, and 500 nM in Spotting buffer (100 mM Phosphate pH 8, 10% glycerol). 1 µl of each dilution was spotted onto an SFB-modified surface. The probe was incubated under a humid environment for 2-16 hours. Surfaces were then washed with water and treated with 0.1% SDS at >37° C. for 2-16 hours to remove loosely adsorbed capture probe. Surfaces were again washed with water, dried, and stored in a nitrogen purged dry box protected from light.

Example 2

Primers and Probes

Primer and probe oligonucleotide sequences were designed using Primer 3 software (http://frodo.wi.mit.edu/cgi-bin/primer3/primer3_www.cgi) with input sequences downloaded from the GenBank genetic sequence repository. The sequences used in these studies are shown in FIG. 9. Reverse primers were modified at their 5'-termini with biotin-TEG (5"-BT) (Glen Research, Sterling, Va.) to facilitate detection of amplified sequences. Target-specific capture probes (CP) were modified on their 5'-termini with a 5'-I-linker (Integrated DNA Technologies, Coralville, Iowa) and iS18 spacer (Glen Research, Sterling, Va.) to facilitate immobilization to surface aldehyde groups with optimized spacing for DNA hybridization. Amplicon sizes in the Examples below were 82, 84, or 116 base pairs for the L, J, and Q mecA amplicons, respectively, and 95 base pairs for the ApoB amplicon.

Example 3

On-Surface HDA Protocol

For on-surface HDA, surfaces were secured in wells of microwell plate using double sided tape. A Master mix was prepared using HDA Universal II kit reagents (BioHelix Corp., Beverly, Mass.) by adding the following (1× concentration): 1× annealing buffer (20 mM Tris-HCl, pH 8.8, 10 mM KCl), 40 mM NaCl, 4 mM MgSO$_4$, 400 µM dNTPs, 3 mM dATP, 0.1 µm each primer pair, 1× helicase enzyme mix and sterile water up to volume. The Master mix was aliquoted (74 µl) onto the surface of each well. Purified or extracted MRSA genomic DNA (1 µl) was added to each reaction and the plate surface was covered with sealing tape (Roche) and incubated at 65° C. (hot plate or incubator) for an appropriate amount of time, usually 45 minutes. Following amplification, the supernatant was removed and surface(s) were washed with wash A (0.1×SSC, 0.1% SDS) followed by wash B (0.1×SSC). Next, a mouse monoclonal anti-biotin antibody conjugated to HRP diluted 1/1000 in 1× hybridization buffer (5×SSC, 0.1% SDS, 0.5% StabilCoat (Surmodics)) was added to the coated support surface(s) and incubated at room temperature for 10 minutes. The surface(s) were then washed with wash B and incubated with 125 µl of TMB at room temperature for 5 minutes. The surface(s) were then washed with water and methanol and allowed to dry.

Example 4

Hybridization of double-stranded DNA targets to surface-immobilized target-specific probes is made possible using helicase to unwind the double-stranded target.

To demonstrate that helicase can sufficiently denature double-stranded DNA templates to create single-stranded regions available for hybridization to target-specific probes, mecA polynucleotide targets from methicillin-resistant *Staphylococcus aureus* DNA were amplified in a microtiter tube (25 µL) for 60 minutes using the mecA L primer set as described in Example 3. The HDA amplified products (or amplicons) were diluted 1/500 in water and hybridized to a thin film biosensor chip (Inverness Medical-Biostar, Inc.) adhered to the bottom of a microtiter plate containing 90 µL of 1× hybridization buffer or 1× IsoAmp II buffer (20 mM Tris-HCl, pH 8.8, 10 mM KCl, 40 mM NaCl, 4 mM MgSO$_4$). For a negative control (Chip A) 10 µL of water was added to a chip containing 1× Hybridization buffer. For a heat denaturation control (chip B), a 10 µl amplicon aliquot was heated to 95° C. for 5 minutes and then added to a chip surface containing 1× Hybridization buffer. For a no denaturation control (Chip C), 10 µL of diluted amplicon was added directly to a chip containing 1× HDA buffer along with 5 µL of the helicase diluent buffer (10 mM KCl, 1 mM Tris-HCl, 0.1 mM DTT, 0.01 mM EDTA, 0.01% TX-100, 5% glycerol pH 7.4 final concentration). For the helicase denatured target sample (Chip D), 5 µL of helicase (150 ng in helicase diluent buffer) was added to the 10 µL of diluted amplicon, and placed onto a chip containing 1× HDA buffer. All surfaces were incubated 15 minutes at 53° C. and then washed with wash A followed by wash B. To each chip, 125 μL of anti-biotin antibody/HRP conjugate diluted 1/1000 in 1× Hybridization buffer was added and incubated at room temperature for 10 minutes. The chips were washed with wash B and then 125 μL of TMB was added. The chips were incubated another 5 minutes, washed with water and methanol and allowed to dry.

As shown in FIG. 1, hybridization of target DNA requires denaturation thereof, as expected. In particular, addition of helicase to the target yielded a positive signal, albeit not as strong as the heat denaturation control. This suggests that helicase may not be as effective as heat in denaturing the sample. It should be noted, however, that the helicase was not incubated at its optimal temperature (65° C.) for this study. Additionally, the sensitivity of target detection is lowered 2-4 fold in 1× HDA buffer compared with 1× Hybridization buffer at 53° C. (data not shown). Nonetheless, this study illustrates that helicase is sufficient to unwind double-stranded targets for hybridization to surface-immobilized probes.

Example 5

Dissociation and detection of hybridized polynucleotide targets from the cationic surface is unexpectedly affected by the ionic strength.

Sequences from the mecA gene in methicillin-resistant *Staphylococcus aureus* were amplified in a microtiter tube (25 μL) for 60 minutes using the mecA L primer set as described in Example 3. Amplicons from an HDA reaction were diluted 1/5000 in 1× Hybridization buffer and annealed to a thin film biosensor chip for 15 minutes at 53° C. Surfaces were washed with wash A and wash B. Then either 100 μl of 1× IsoAmp II buffer or 1× Hybridization buffer was added and incubated at various temperatures. Reactions were stopped at various times by washing with wash A followed by wash B. To each chip, 125 μL of anti-biotin antibody/HRP conjugate diluted 1/1000 in 1× Hybridization buffer was added and incubated at room temperature for 10 minutes. The chips were washed with wash B and then 125 μL of TMB was added. The chips were incubated another 5 minutes, washed with water and methanol and allowed to dry.

Figure 2:
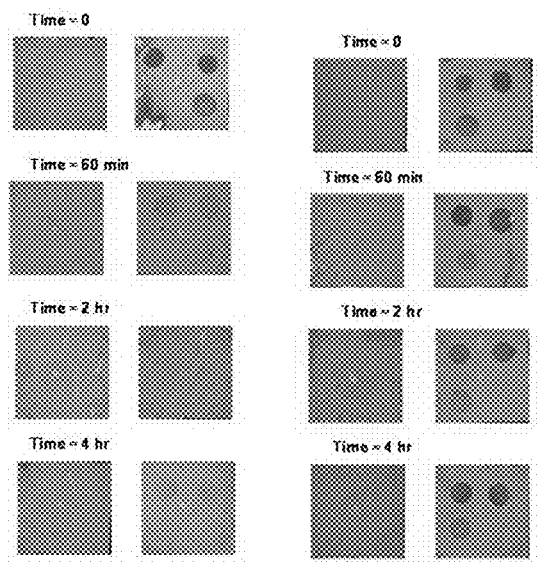
FIG. 2 depicts more stable binding of amplified polynucleotide targets to the coated solid support in low salt conditions (1× IsoAmp II) than in high salt conditions (1× Hyb).
Figure 2:
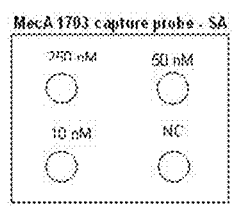

As shown in FIG. 2, at 58.5° C. surface-bound target DNA rapidly dissociated from the chip surface ($t_{1/2}$~30 minutes) in the presence of the high salt 1× Hybridization buffer (containing 825 mM monovalent cation). In contrast, there was still a significant fraction of target remaining in the presence of 1× IsoAmpII buffer (containing 54 mM monovalent cation), even after 4 hours at 58.5° C. Additional experiments conducted over a range of temperatures (53° C. to 64° C.) confirmed that dissociation of target DNA from the surface was more rapid at higher temperatures in 1× Hybridization buffer, as expected for DNA duplexes ($t_{1/2}$~240 minutes at 53° C. and <<30 minutes at 64° C., data not shown). Rates of dissociation from the coated support surface (as reflected by detectable signal), while not quantitatively determined here, appear to be similar to reported literature values. In contrast, dissociation of target DNA from the surface was much slower in the lower ionic strength IsoAmp II buffer under otherwise equal conditions ($t_{1/2}$>>360 minutes at 53° C. and >>240 minutes at 58.5° C., data not shown.

The conventional expectation would be for DNA duplexes to dissociate faster in lower ionic strength buffers exhibiting less charge stabilization. Therefore, the data above suggests that the surface with a cationic character is playing a role in dissociation of target DNA from the surface. While not wishing to be bound by theory, it is believed that under high salt conditions, surface cations are shielded from interacting with (and stabilizing) the hybridized polynucleotide targets. Accordingly, the polynucleotide targets can more freely dissociate from the surface. Under low salt HDA reaction conditions, the cations may retain their ability for electrostatic interaction with the backbone of the polynucleotide target DNA, slowing or preventing its dissociation from the surface even though the target may be no longer hybridized to the surface-immobilized probe.

Example 6

Doubling Time for MRSA Primers in Solution

A series of HDA reactions were performed using a range of genomic MRSA (ATCC) input DNAs (100-1,000,000 copies) in a reaction mixture containing 1× annealing buffer (20 mM Tris-HCl, pH 8.8, 10 mM KCl) (BioHelix), 40 mM NaCl, 4 mM MgSO4, 400 μm dNTPs, 3 mM ATP, 0.1 μm each primer, 1× helicase enzyme mix (BioHelix), 0.2× EvaGreen (Biotium, Inc.). Samples were placed in a Roche LightCycler 480 optical plate, covered with sealing tape and placed into the Roche LightCycler 480. Plates were incubated at 65° C. and data was collected every 60 seconds. EvaGreen is a double strand-specific dye conferring increases in fluorescence as a function of amplification. Melt Curve analysis was performed after the amplification to verify that a full-length amplicon of expected Tm was produced. Amplification fidelity was further confirmed by hybridization to target-specific probes immobilized onto silicon chips as described above. Dye incorporation was evaluated by plotting the time to detectable signal (CP) against copy number of input genomic DNA. The slope of the curves yields yield doubling times (time for primer pair to create a copy) characteristic for each primer set. This analysis provides a reasonable approximation of the expected amount of amplicon present at any given time. Given that there is likely a bit of a lag phase to overcome in the early stages of the HAD reaction, actual doubling rates may be somewhat faster than the averaged doubling times determined herein.

Figures 3A, 3B:
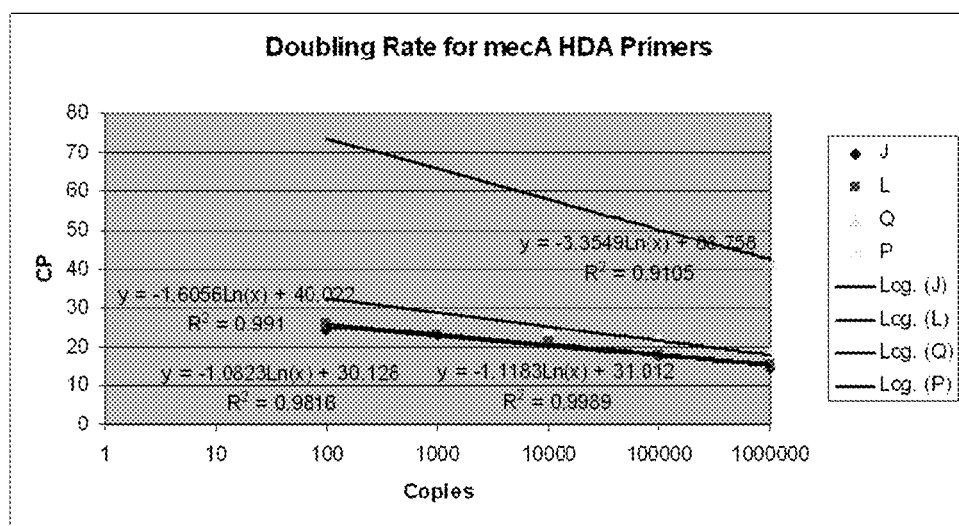
FIG. 3 depicts representative doubling times (FIG. 3A) and doubling rates (FIG. 3B) for HDA amplicons produced using selected primer sets (J, L, Q, and P) directed to the mecA gene specifying methicilin resistance in *Staphylococcus*.

FIGS. 3A and 3B illustrate representative amplification data for primer sets targeting the mecA gene in methicillin-resistance in *Staphylococcus*. The tested primer pairs were found to exhibit doubling times in solution ranging from about 1-3 minutes. Those with the shortest doubling times (and found to be specific for target amplification) were chosen for further assay development.

Example 7

Determination of the Effect of the Chip on HDA Amplification Efficiency

HDA reactions were set-up in 1.7 mL microcentrifuge tubes or on a chip with 2000 copies of purified human DNA (Promega) as input for amplification. Reactions were allowed to proceed for various amounts of time and the reactions were stopped. Reactions from both sample sets were applied to a 2% agarose gel stained with ethidium bromide.

Both sets of reactions show clearly visible bands of the correct size on the gel after 30 minutes amplification time. There appears to be no adverse effect on amplification efficiency from the chip1. On-chip amplicons are revealed as a single band on the gel and the bands at equal time points are more intense.

Example 8

Figure 4:
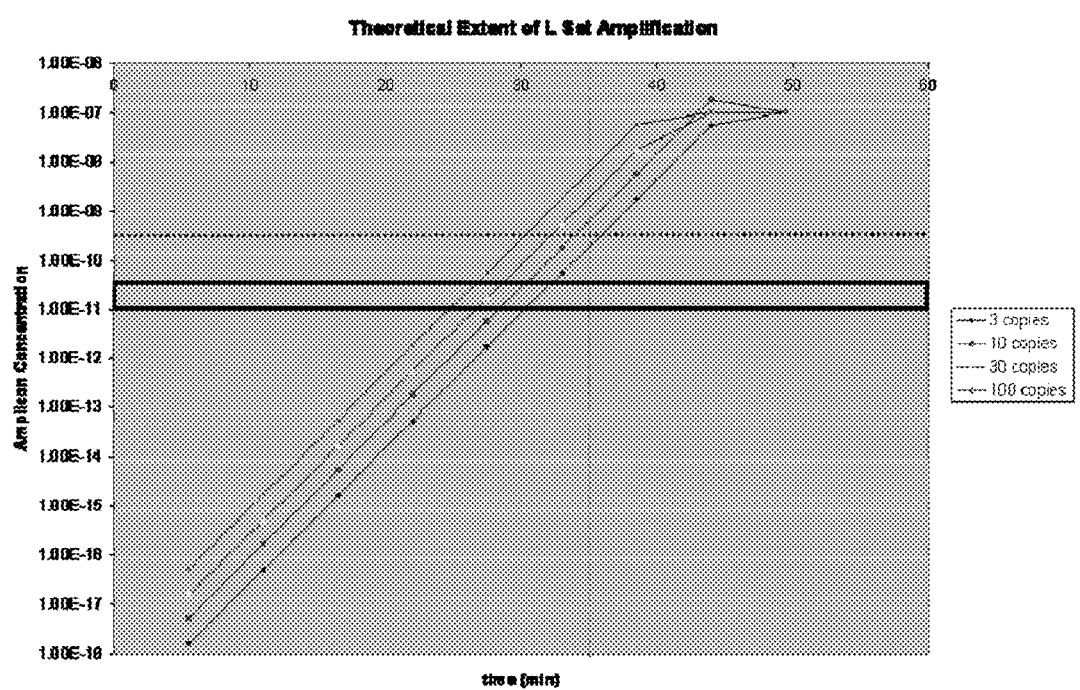
FIG. 4 depicts a calculation of predicted time to result (TTR) on silicon chips based on the lower limit of detection (LLOD) and amplicon doubling times.

Calculation of Theoretical TTRs Based on Theoretical Chip LLODs and Calculated Doubling Times The calculated primer doubling times in solution (e.g., 1.1 minutes for the "L" primer set) were used to calculate a theoretical time to result (TTR) for a chip not interfering with amplification/detection based on chip LLODs measured at 10-30 pM input DNA (amplicon) under HDA temperature (65° C.) and buffer conditions. A plot of the amount of amplicon present as a function of amplification time is shown in FIG. 4 below. A bolded box brackets the limit of sensitivity for a given target-specific probe set and a dashed line shows the amount that is 10-fold above the LLOD (lower limit of detection). A vertical line approximates the time to detectable signal for 10 copies of target as input into the HDA reaction. The results show that from as few as 10 copies of input DNA, detectable levels of amplicon can be obtained by ~30 minutes, further producing 10-fold level of the detection threshold by 38 minutes.

Example 9

Detection of HDA Amplification Products on Silicon Chips (LLOD)

Figure 5:
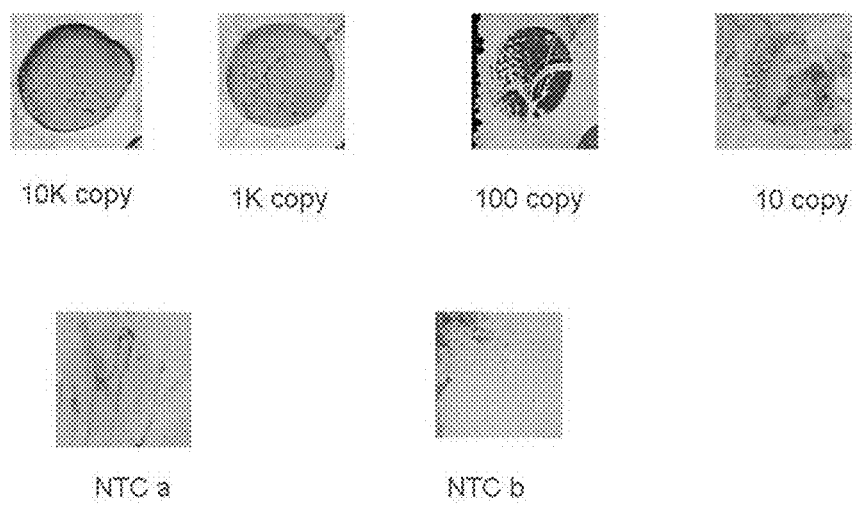
FIG. 5 depicts a dose response analysis to calculate the lower limit of detection (LLOD) of MRSA DNA amplified by HDA and hybridized to coated silicon chips.

To determine the lower limit of detection (LLOD) corresponding to on-chip HDA amplification/detection of MRSA DNA, a dose response analysis of MRSA DNA amplification was performed using the protocol described in Example 3. Sequences in the mecA gene from purified methicillin-resistant *Staphylococcus aureus* genomic DNA (ATCC, strain #11632) were amplified using the "L" primer set described in Example 2 and depicted in FIG. 9. The dose response for genomic input DNA ranging from 0 to 10,000 copies was tested. Amplification reactions were incubated for 45 minutes at 64° C. on "rough-side" silicon chips containing a surface immobilized mecA-specific capture probe (mecA1703 CP, FIG. 9). The representative data in FIG. 5 includes negative controls NTC A and NTC B. The results show that the LLOD is 10 copies of target DNA on the chip. The LLOD result was further reproduced in experiments amplifying the human ApoB gene and the cfb gene of *Streptococcus agalactiae*.

Example 10

Detection of HDA Amplification Products on Silicon Chips (TTR)

Figure 6:
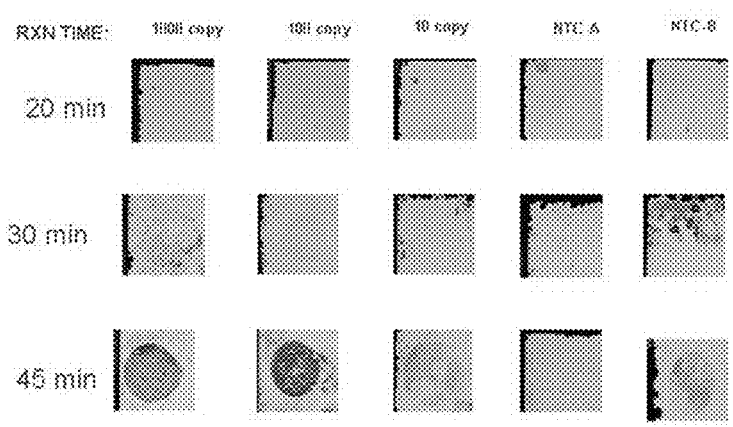
FIG. 6 depicts a time to result (TTR) analysis of MRSA DNA amplified by HDA and hybridized to coated silicon chips.

To determine the time necessary for amplifying MRSA genomic DNA to detectable levels (time to result, TTR), HDA reactions were performed using mecA-specific primers in the presence of varying amounts (0-1000 sequence copies) of purified genomic DNA from methicillin-resistant *Staphylococcus aureus* applied to the "rough-side" silicon chip coated with mecA-specific capture probe 1703 as described in Example 3. Signals on the chip were measured at various time points by washing the chip to stop the reaction prior to addition of the detection reagents. Representative data is shown in FIG. 6. With 100 sequence copies of MRSA target DNA, the chip yielded a detectable signal after 30 minutes; 10 copies of input yielded a detectable signal after 45 minutes. These results are generally consistent with the theoretical model in Example 8 predicting detectability of 100 copies by 27-30 minutes and 10 copies by 30-33 minutes. (To more accurately assess HDA performance for 10 copies relative to the theoretical model, more time points may be required around 30 minutes). This data suggests that on-chip HDA amplification can perform near its predicted limits under conditions wherein the chip does not adversely affect amplification efficiency. This data also suggests that HDA does not appear to show an extended lag phase at the onset of amplification slowing the time to detectable result. To the extent that there may be such a lag phase, however, the primers would generate faster than predicted doubling times.

Example 11

Detection of HDA Amplification Products on Thin Film Biosensor Chips

Figure 7:
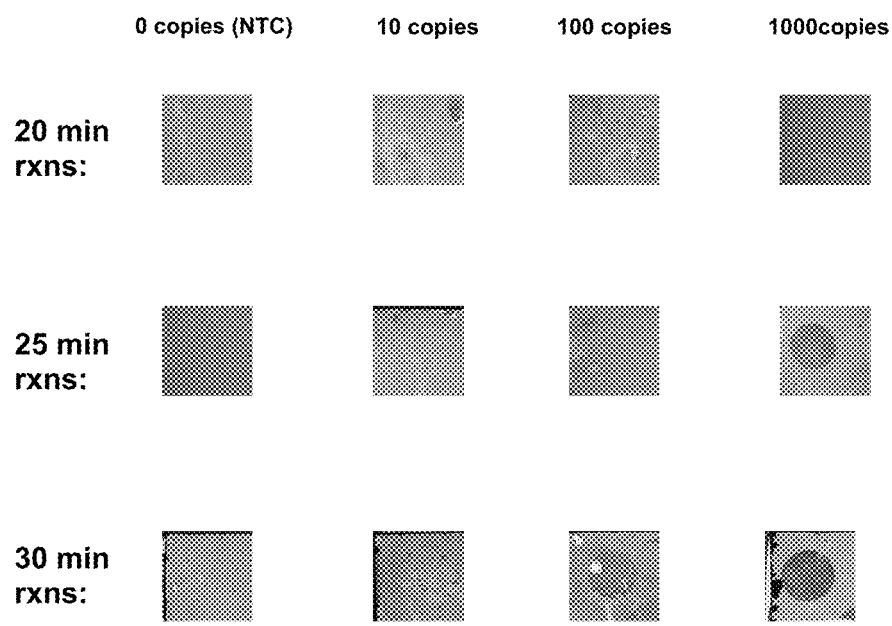
FIG. 7 depicts an analysis of direct, on-chip HDA detection to a thin film biosensor chip (On-chip).

To test HDA on-chip amplification/detection on another visual detection medium, we utilized a thin film biosensor chip containing immobilized mecA probes (1703) for direct visual detection according to the method described in Examples 3 and 10. On-chip detection times were similar to the rough side silicon chip used in Example 10. As shown in FIG. 7, amplification of 100 copies of genomic DNA produced detectable signals by 30 minutes, consistent with the results observed using the rough-side chips. Coated silicon supports may therefore provide a flexible platform for on-chip HDA amplification and detection.

Example 12

Detection of mecA Gene Sequences from Blood Culture Isolates Using On-Chip HDA Detection in Relation to Varying Surface Treatments Blood was drawn (~10 mL) and placed into a BACTEC blood culture bottle. The bottle was then seeded with ~1,000,000 CFU of methicillin-resistant *Staphylococcus aureus* (ATCC strain #11632) plated onto blood agar and grown at 37° C. overnight. The blood culture bottle was incubated in a BACTEC instrument until the alarm sounded, indicating that the bottle was positive for bacterial growth. Dilution plating revealed the presence of about $10^8$ to $10^9$ organisms per mL at the time the alarm sounded. Aliquots (10 μl) were removed from a MRSA+BACTEC blood culture bottle and added to 3 μl of 1M NaOH to lyse erythrocytes. Next, 87 μl of an extraction mix was added (10 mM Tris pH 7, 50 units achromopeptidase (ACP, Sigma)) and incubated for 10 minutes at room temperature prior to boiling the treated sample to inactivate the ACP. From the lysed sample 1 μl was then subjected to on-chip HDA reaction on thin film biosensor chips for 40 minutes essentially as described in Example 3. Negative controls included lysis of 10 μL bacteria-free blood culture.

Four different thin film biosensor chips were used: (1) a chip that was aged 6 months after attachment of the probe not subsequently treated to block remaining reactive groups (Aged); (2) a freshly made chip not subsequently treated to block remaining reactive groups (Un-blocked); (3) a freshly made chip from the same batch, treated with 100 μm NHS-acetate (Pierce) to block easily accessible surface amines NHS-Ac block); and (4) a freshly made chip from the same batch, treated with 100 μm acetic anhydride (Aldrich) to block easily accessible surface amines (AcAn block).

Figure 8:
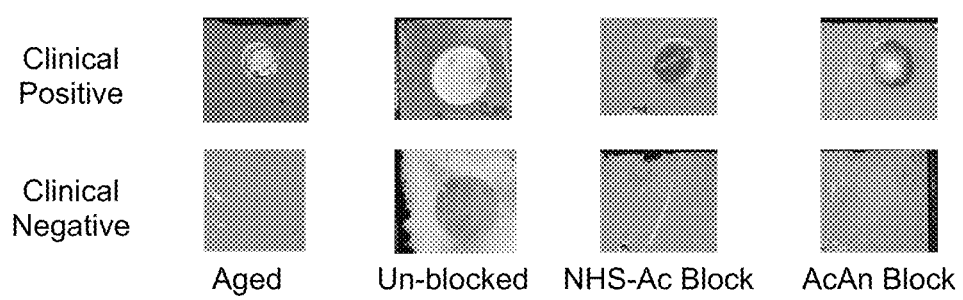
FIG. 8 depicts detection of HDA amplicons from a blood culture isolate on (left to right): an aged chip (Aged), an un-blocked chip (Un-blocked), an N-hydroxysuccinimidyl (NHS) acetate blocked chip (NHS-Ac block), and an acetic anhydride blocked chip (AcAn block).

Representative results are shown in FIG. 8. Clearly detectable signal was observed on all chips. The negative controls were devoid of signal, indicating that the matrix is not interfering with amplification/detection except in the case of the un-blocked freshly prepared chip, which showed evidence of surface passivation, or non-specific binding, by components in the blood culture extract, including achromopeptidase extracted bacterial cells, blood components and/or culture media. These data show that performance on a coated cationic surface can be improved by aging or other treatments serving to block at least a proportion of the free amines.

It appears that surfaces may become more hydrophobic over time with poly-(lys, phe) coatings on silicon or thin film biosensors as measured by increased contact angle in a goniaometer (data not shown). This suggests that significant diffusion occurs over time, changing the accessibility of amines. While this doesn't appear to harm the ability to immobilize capture probes, it is beneficial to control non-specific interactions involving components in blood culture samples, for example. As a method to "accelerate" this diffusion process, accessible free amines can be modified with NHS-acetate or acetic anhydride. Although these methods can block significant amounts of accessible amines, blockage of all amines is not complete, leaving others available to interact locally with immobilized target sequences so as to slow their diffusion from the surface under low ionic strength conditions (<50 mM $Na^+$).

It is intended that the foregoing detailed description be regarded as illustrative rather than limiting, and that it be understood that it is the following claims, including all equivalents, that are intended to define the spirit and scope of this invention.

The invention claimed is:

1. A method for detecting the presence or absence of a polynucleotide target in a sample, comprising:
   a. providing a coated, solid support comprising (i) a solid support, (ii) a coating layer comprising at least one polycationic polymer, and (iii) a plurality of target-specific probes attached to the coating layer;
   b. contacting the coated, solid support with a sample suspected of having a polynucleotide target and a reaction medium comprising helicase, DNA polymerase, target-specific DNA primers, and dNTPs, wherein the reaction medium has a monovalent cation concentration between about 10 mM and about 100 mM;
   c. heating the sample and reaction medium to produce isothermally amplified polynucleotide targets that are simultaneously captured by target-specific probes on the coated, solid support;
   d. detecting the presence or absence of the polynucleotide target from amplified polynucleotide targets bound to the target-specific probes.

2. The method of claim 1, wherein step (c) comprises incorporating a label into the amplified polynucleotide targets.

3. The method of claim 2, wherein step (d) comprises binding an enzyme to the label and generating reaction products that are detectable on the surface of the coated, solid support.

4. The method of claim 2, wherein step (d) comprises binding an anti-label, antibody-enzyme conjugate to the label.

5. The method of claim 2, wherein step (d) comprises binding an enzyme to the label and generating precipitable reaction products that are detectable on a surface of the coated, solid support under visible light.

6. The method of claim 1, wherein the solid support is formed from a member of the group consisting of silicon, plastic, glass, and membrane.

7. The method of claim 1, wherein the solid support comprises a silicon wafer or chip.

8. The method of claim 1, wherein the polycationic polymer is selected from one or more of the group consisting of polylysine, poly(lys-phe), poly(lys-tyr), poly(lys-trp), poly(arg-trp), and poly(arg-pro-tyr).

9. The method of claim 1, wherein the polycationic polymer is attached to the solid support.

10. The method of claim 1, wherein the coating layer comprises a compound selected from one or more of the group consisting of a cationic silane, a cationic siloxane, or a cationic derivative thereof.

11. The method of claim 1, wherein the coating layer comprises or is attached to a compound selected from one or more of the group consisting of aminopropyltrimethoxysilane, aminopropyltriethoxysilane, amino-functional organopolylsiloxanes, and amino-functional siloxane alkoxylates.

12. The method of claim 1, wherein the coating layer comprises an attachment layer.

13. The method of claim 1, wherein the plurality of target-specific probes are attached to an attachment layer comprising a coating of coupling agents deposited on a surface of the solid support.

14. The method of claim 1, wherein the plurality of target-specific probes comprise at least one modified oligonucleotide containing a structural element reducing binding of an isothermal amplification enzyme to an oligonucleotide bound to the polynucleotide target.

15. The method of claim 1, wherein the plurality of target-specific probes comprise at least one modified oligonucleotide containing a structural element reducing enzymatic denaturation of the oligonucleotide bound to the polynucleotide target.

16. The method of claim 1, wherein the plurality of target-specific probes comprise at least one probe having at least one terminus blocked to reduce recognition by an isothermal amplification enzyme.

17. The method of claim 1, wherein the plurality of target-specific probes comprise at least one probe modified or blocked to reduce recognition by a helicase.

18. The method of claim 1, wherein the plurality of target-specific probes comprise at least one probe comprising a backbone having at least one neutral charge.

19. The method of claim 1, wherein the plurality of target-specific probes comprise at least one probe comprising a methylphosphonate backbone.

20. The method of claim 1, wherein the plurality of target-specific probes comprise at least one probe comprising a peptide nucleic acid.

21. The method of claim 1, wherein the plurality of target-specific probes comprise at least one probe comprising a 2'-O-methyl linkage.

22. The method of claim 1, wherein the plurality of target-specific probes comprise at least one probe comprising a locked nucleic acid.

23. The method of claim 1, wherein the sample comprises a purified polynucleotide or extract from an animal cell, microbial cell, or combinations thereof.

24. The method of claim 1, wherein the reaction medium also comprises single-stranded binding protein.

* * * * *

SEQUENCE LISTING

```
<160> NUMBER OF SEQ ID NOS: 11

<210> SEQ ID NO 1
<211> LENGTH: 27
<212> TYPE: DNA
<213> ORGANISM: Artificial
<220> FEATURE:
<223> OTHER INFORMATION: primer; mecA L FWD

<400> SEQUENCE: 1
tggatagacg tcatatgaag gtgtgct                                27

<210> SEQ ID NO 2
<211> LENGTH: 27
<212> TYPE: DNA
<213> ORGANISM: Artificial
<220> FEATURE:
<223> OTHER INFORMATION: primer; mecA L REV
<220> FEATURE:
<221> NAME/KEY: misc_feature
<222> LOCATION: (0)..(1)
<223> OTHER INFORMATION: 5'-BT: biotinTEG Phosphoramidite; 5'-biotin
      modification

<400> SEQUENCE: 2
attatggctc aggtactgct atccacc                                27

<210> SEQ ID NO 3
<211> LENGTH: 27
<212> TYPE: DNA
<213> ORGANISM: Artificial
<220> FEATURE:
<223> OTHER INFORMATION: primer; mecA J FWD

<400> SEQUENCE: 3
tggatagacg tcatatgaag gtgtgct                                27

<210> SEQ ID NO 4
<211> LENGTH: 26
<212> TYPE: DNA
<213> ORGANISM: Artificial
<220> FEATURE:
<223> OTHER INFORMATION: primer; mecA J REV
<220> FEATURE:
<221> NAME/KEY: misc_feature
<222> LOCATION: (0)..(1)
<223> OTHER INFORMATION: 5'-BT: biotinTEG Phosphoramidite; 5'-biotin
      modification

<400> SEQUENCE: 4
tgattatggc tcaggtactg ctatcc                                 26
```

```
<210> SEQ ID NO 5
<211> LENGTH: 25
<212> TYPE: DNA
<213> ORGANISM: Artificial
<220> FEATURE:
<223> OTHER INFORMATION: probe; mecA1703 CP
<220> FEATURE:
<221> NAME/KEY: misc_feature
<222> LOCATION: (0)..(1)
<223> OTHER INFORMATION: 5'ILink12: 5'-I-linker (covalent attachment
      chemistry for oligonucleotides)
<220> FEATURE:
<221> NAME/KEY: misc_feature
<222> LOCATION: (0)..(1)
<223> OTHER INFORMATION: iS18: Int Spacer 18 (internal oligonucleotide
      spacer)

<400> SEQUENCE: 5
caagtgctaa taattcacct gtttg                                           25

<210> SEQ ID NO 6
<211> LENGTH: 27
<212> TYPE: DNA
<213> ORGANISM: Artificial
<220> FEATURE:
<223> OTHER INFORMATION: primer; mecA Q FWD

<400> SEQUENCE: 6
caaactacgg taacattgat cgcaacg                                         27

<210> SEQ ID NO 7
<211> LENGTH: 25
<212> TYPE: DNA
<213> ORGANISM: Artificial
<220> FEATURE:
<223> OTHER INFORMATION: primer; mecA Q REV
<220> FEATURE:
<221> NAME/KEY: misc_feature
<222> LOCATION: (0)..(1)
<223> OTHER INFORMATION: 5'-BT: biotinTEG Phosphoramidite; 5'-biotin
      modification

<400> SEQUENCE: 7
atgctttggt ctttctgcat tcctg                                           25

<210> SEQ ID NO 8
<211> LENGTH: 22
<212> TYPE: DNA
<213> ORGANISM: Artificial
<220> FEATURE:
<223> OTHER INFORMATION: probe; mecA1653 CP
<220> FEATURE:
<221> NAME/KEY: misc_feature
<222> LOCATION: (0)..(1)
<223> OTHER INFORMATION: 5'ILink12: 5'-I-linker (covalent attachment
      chemistry for oligonucleotides)
<220> FEATURE:
<221> NAME/KEY: misc_feature
<222> LOCATION: (0)..(1)
<223> OTHER INFORMATION: iSp18: Int Spacer 18 (internal oligonucleotide
      spacer)

<400> SEQUENCE: 8
aaacaaacta cggtaacatt ga                                              22

<210> SEQ ID NO 9
<211> LENGTH: 33
<212> TYPE: DNA
<213> ORGANISM: Artificial
<220> FEATURE:
<223> OTHER INFORMATION: primer; APOB4 rev
```

```
<220> FEATURE:
<221> NAME/KEY: misc_feature
<222> LOCATION: (0)..(1)
<223> OTHER INFORMATION: 5'-BT: biotinTEG Phosphoramidite; 5'-biotin
      modification

<400> SEQUENCE: 9
cagtgtatct ggaaagccta caggacacca aaa                              33

<210> SEQ ID NO 10
<211> LENGTH: 26
<212> TYPE: DNA
<213> ORGANISM: Artificial
<220> FEATURE:
<223> OTHER INFORMATION: primer; APOB FWD 3

<400> SEQUENCE: 10
cttcatgtga gccaaagatg ctgaac                                      26

<210> SEQ ID NO 11
<211> LENGTH: 20
<212> TYPE: DNA
<213> ORGANISM: Artificial
<220> FEATURE:
<223> OTHER INFORMATION: probe; APOB-CP1
<220> FEATURE:
<221> NAME/KEY: misc_feature
<222> LOCATION: (0)..(1)
<223> OTHER INFORMATION: 5'ILink12: 5'-I-linker (covalent attachment
      chemistry for oligonucleotides)
<220> FEATURE:
<221> NAME/KEY: misc_feature
<222> LOCATION: (0)..(1)
<223> OTHER INFORMATION: iSp18: Int Spacer 18 (internal oligonucleotide
      spacer)

<400> SEQUENCE: 11
aatttggcct tcatgtgagc                                             20
```